United States Patent [19]

Jaunin

[11] 4,122,265
[45] Oct. 24, 1978

[54] DERIVATIVES OF 3-PHENYLISOINDOLE-1-CARBOXYLIC ACID

[75] Inventor: Roland Jaunin, Basel, Switzerland

[73] Assignee: Hoffmann-La Roche Inc., Nutley, N.J.

[21] Appl. No.: 789,905

[22] Filed: Apr. 22, 1977

[30] Foreign Application Priority Data

May 21, 1976 [CH] Switzerland .......................... 6454/76
Mar. 8, 1977 [CH] Switzerland .......................... 2876/77

[51] Int. Cl.² ........................................... C07D 413/12
[52] U.S. Cl. .............................. 544/143; 260/239 BD;
260/239 BF; 260/239 E; 260/243.3;
260/293.61; 260/293.76; 260/326.1;
260/326.43; 260/558 R; 260/558 P; 260/559 R;
544/144; 544/373; 544/397; 424/248.54;
424/250; 424/267; 424/274

[58] Field of Search .............................. 544/143, 144;
260/326.1, 293.61, 268 BC

[56] References Cited
U.S. PATENT DOCUMENTS 3,996,374  12/1976  Jaunin .............................. 260/326.1

Primary Examiner—Herny R. Jiles
Assistant Examiner—R. W. Ramsuer
Attorney, Agent, or Firm—George M. Gould; William G. Isgro

[57] ABSTRACT

Isoindole derivatives of the formula

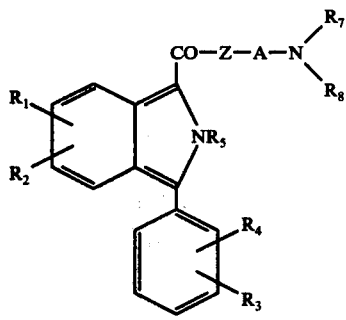

wherein A, Z, $R_1$, $R_2$, $R_3$, $R_4$, $R_5$, $R_6$, $R_7$, $R_8$ and $n$ are as hereinafter set forth, as well as intermediates, are described. The end products of formula I are useful as appetite-suppressants.

37 Claims, No Drawings

DERIVATIVES OF 3-PHENYLISOINDOLE-1-CARBOXYLIC ACID

BRIEF SUMMARY OF THE INVENTION

The invention relates to isoindole derivatives of the formula

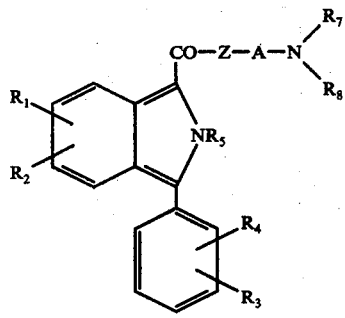

I wherein A is alkylene of 2-8 carbon atoms; Z is oxygen or a group of the formula $-NR_6$; $R_1$, $R_2$, $R_3$ and $R_4$, independently, are hydrogen, halogen, alkyl, alkoxy or trifluoromethyl; $R_5$ and $R_6$, independently, are hydrogen or alkyl; and $R_7$ and $R_8$, independently, are hydrogen, alkyl, cycloalkyl, cycloalkylalkyl, alkoxyalkyl, aryl or aralkyl, or $R_7$ and $R_8$, when taken together, are a group of the formula $-(CH_2)_n-$, wherein $n$ is an integer of from 2-7, or $NR_7R_8$ is a 5-membered or 6-membered saturated heterocyclic group containing an oxygen atom or an additional nitrogen atom which may be substituted with alkyl or hydroxyalkyl, or a pharmaceutically acceptable acid addition salt thereof.

In another aspect, the invention relates to intermediates of formulas II, IV, V, VII, X, XI and XII, as set forth hereinafter in the specification.

DETAILED DESCRIPTION OF THE INVENTION

The invention relates to compounds characterized by the formula

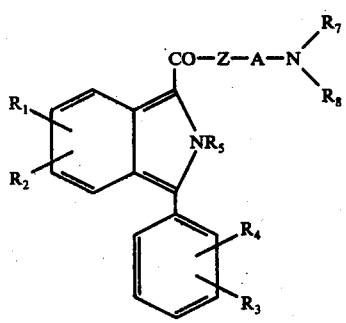

I wherein A is alkylene of 2-8 carbon atoms; Z is oxygen or a group of the formula $-NR_6$; $R_1$, $R_2$, $R_3$ and $R_4$, independently, are hydrogen, halogen, alkyl, alkoxy or trifluoromethyl; $R_5$ and $R_6$, independently, are hydrogen or alkyl; and $R_7$ and $R_8$, independently, are hydrogen, alkyl, cycloalkyl, cycloalkylalkyl, alkoxyalkyl, aryl or aralkyl, or $R_7$ and $R_8$ when taken together are a group of the formula $-(CH_2)_n-$, wherein $n$ is an integer of from 2-7, or $-NR_7R_8$ is a 5-membered or 6-membered saturated heterocyclic group containing an oxygen atom or an additional nitrogen atom which may be substituted with alkyl or hydroxyalkyl, or a pharmaceutically acceptable acid addition salt thereof.

As used herein, the term "alkyl" or "lower alkyl", alone or in combination, such as, in "alkoxy," denotes a straight-chain or branched-chain saturated hydrocarbon group containing 1 to 6 carbon atoms such as methyl, ethyl, propyl, isopropyl, butyl or the like. The term "alkylene" or "lower alkylene" denotes a straight-chain or branched-chain alkylene group containing 1 to 6 carbon atoms, such as, for example, ethylene, methylethylene, trimethylene, tetramethylene and the like. The term "cycloalkyl," alone or in combination, includes $C_3-C_6$-cycloalkyl residues, such as, cyclopropyl, cyclobutyl, cyclopentyl or cyclohexyl. Exemplary of 5-membered or 6-membered saturated heterocyclic groups are morpholino, N-methylpiperazino, piperazino or the like. The term "halogen" denotes fluorine, chlorine, bromine and iodine. The term "aryl" denotes mononuclear or polynuclear aromatic groups in which one or more of the hydrogen atoms may be replaced by alkyl, alkoxy or halogen substituents, examples of such aryl groups are phenyl, halophenyl, methoxyphenyl or the like. The term "leaving atom or group" includes halogen, arylsulfonyloxy, such as, tosyloxy and alkylsulfonyloxy, such as, mesyloxy. The term "protecting group" includes acyl groups, such as, alkanoyl derived from an aliphatic carboxylic acid of 1 to 7 carbon atoms, for example, formyl, acetyl, propionyl or the like; carbalkoxy, such as, carbomethoxy; aralkoxycarbonyl, such as, carbobenzoxy; and benzyl.

In a preferred embodiment of the invention, $R_1$, $R_2$, $R_3$ and $R_4$, independently, are hydrogen, halogen or trifluoromethyl. In a more preferred embodiment $R_4$ is hydrogen and $R_1$ is chlorine, fluorine, or trifluoromethyl. Also, in a more preferred embodiment, $R_2$ and $R_3$, independently, are hydrogen, chlorine or fluorine. Furthermore, isoindole derivatives of formula I wherein $R_5$ and $R_6$, independently are hydrogen, alkyl, particularly methyl, are preferred. In yet another preferred embodiment, A is ethylene or trimethylene; $R_7$ and $R_8$, independently, are alkyl, preferably ethyl or isopropyl.

As is evident from the foregoing, particularly preferred isoindole derivatives provided by the present invention are those wherein $R_4$ is hydrogen, $R_1$ is chlorine, fluorine or trifluoromethyl, $R_2$ and $R_3$, independently, are hydrogen, chlorine or fluorine, $R_5$ and $R_6$, independently, are hydrogen or methyl, A is ethylene or trimethylene and $R_7$ and $R_8$, independently, are ethyl or isopropyl.

Most preferred compounds of formula I are:
3-(p-chlorophenyl)isoindole-1-carboxylic acid [2-(diethylamino)ethyl]amide,
5-chloro-3-(p-chlorophenyl)isoindole-1-carboxylic acid [2-(diethylamino)ethyl]amide and
5-chloro-3-phenylisoindole-1-carboxylic acid 3-(diethylamino)propyl ester.

Other preferred compounds of formula I are:
5-chloro-3-phenylisoindole-1-carboxylic acid [2-(diethylamino)ethyl]amide,
5,7-dichloro-3-phenylisoindole-1-carboxylic acid [2-(diethylamino)ethyl]amide,
5-chloro-3-(o-fluorophenyl)isoindole-1-carboxylic acid [2-(diethylamino)ethyl]amide,
5-chloro-3-phenylisoindole-1-carboxylic acid [3-(diethylamino)propyl]amide,
5-chloro-3-phenylisoindole-1-carboxylic acid [3-dimethylamino)propyl]amide, 5-chloro-3-phenylisoindole-1-carboxylic acid (2-morpholinoethyl)amide,
5-chloro-3-phenylisoindole-1-carboxylic acid [2-(1-pyrrolidinyl)ethyl]amide,
5-chloro-3-phenylisoindole-1-carboxylic acid (2-piperidinoethyl)amide,
5-chloro-3-phenylisoindole-1-carboxylic acid [3-(4-methyl-1-piperazinyl)propyl]amide,
5-chloro-2-methyl-3-phenylisoindole-1-carboxylic acid [2-(diethylamino)ethyl]methylamide,
5-chloro-2-methyl-3-phenylisoindole-1-carboxylic acid [2-(diethylamino)ethyl]amide,
2-ethyl-5-chloro-3-phenylisoindole-1-carboxylic acid [2-(diethylamino)ethyl]amide,
5-chloro-3-phenylisoindole-1-carboxylic acid [2-(diethylamino)ethyl]methylamide,
5-chloro-2-methyl-3-phenylisoindole-1-carboxylic acid (3-aminopropyl)amide,
5-chloro-2-methyl-3-phenylisoindole-1-carboxylic acid (3-morpholinoethyl)methylamide,
5-chloro-2-methyl-3-phenylisoindole-1-carboxylic acid [4-(isopropylamino)pentyl]amide,
5-chloro-3-phenylisoindole-1-carboxylic acid 2-morpholinoethyl ester,
5-chloro-3-phenylisoindole-1-carboxylic acid 2-(dimethylamino)ethyl ester,
5-chloro-3-phenylisoindole-1-carboxylic acid 2-(diethylamino)ethyl ester and
5-chloro-3-phenylisoindole-1-carboxylic acid [3-(methylamino)propyl]amide.

The isoindole derivatives, that is, the compounds of formula I and their pharmaceutically acceptable acid addition salts, can be obtained by (a) to prepare compounds of formula I, with the proviso that when $R_4$ is hydrogen, then Z is oxygen or the group of the formula —NH—, reacting a compound of the formula

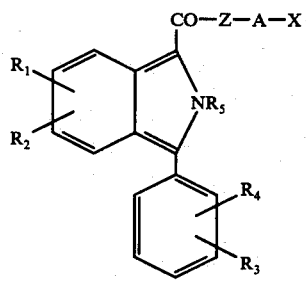

wherein A, Z, $R_1$, $R_2$, $R_3$, $R_4$ and $R_5$ are as previously described and X is a leaving atom or group, with the proviso that when $R_5$ is hydrogen, then Z is an oxygen atom or the group of the formula —NH—, with an amine of the formula

wherein $R_7$ and $R_8$ are as previously described, or (b) to prepare compounds of formula I wherein Z is a group of the formula —$NR_6$—; and $R_7$ and $R_8$, independently, are alkyl, cycloalkyl, cycloalkylalkyl, alkoxyalkyl, aryl or aralkyl, or $R_7$ and $R_8$, when taken together, are a group of the formula —$(CH_2)_n$— wherein $n$ is an integer of from 2-7, or —$NR_7R_8$ is a 5-membered or 6-membered saturated heterocyclic group containing oxygen or an additional nitrogen substituted with alkyl and A, $R_1$, $R_2$, $R_3$, $R_4$, $R_5$ and $R_6$ are as previously described, reductively aminating a compound of the formula

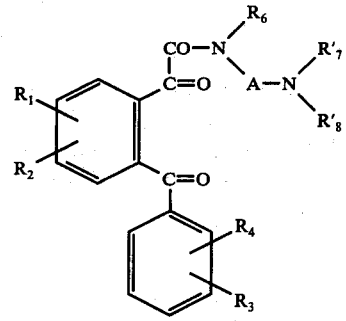

wherein A, $R_1$, $R_2$, $R_3$, $R_4$ and $R_6$ are as previously described, and $R'_7$ and $R'_8$, independently, are alkyl, cycloalkyl, cycloalkylalkyl, alkoxyalkyl, aryl or aralkyl, or $R'_7$ and $R'_8$, when taken together, are a group of the formula —$(CH_2)_n$—, wherein $n$ is an integer of from 2-7, or —$NR'_7R'_8$ is a 5-membered or 6-membered saturated heterocyclic group containing oxygen or an additional nitrogen substituted with alkyl, with an amine of formula III, wherein $R_7$ is hydrogen and $R_8$ is hydrogen or alkyl, or (c) to prepare compounds of formula I wherein Z is a group of the formula —$NR_6$—, $R_5$ is alkyl, and $R_7$ and $R_8$, independently, are alkyl, cycloalkyl, cycloalkylalkyl, alkoxyalkyl, aryl or aralkyl, or $R_7$ and $R_8$, when taken together, are a group of the formula —$(CH_2)_n$—, wherein $n$ is an integer of from 2-7, or —$NR_7R_8$ is 5-membered or 6-membered saturated heterocyclic group containing oxygen or an additional nitrogen substituted with alkyl and A, $R_1$, $R_2$, $R_3$, $R_4$ and $R_6$ are as previously described, reacting a compound of the formula

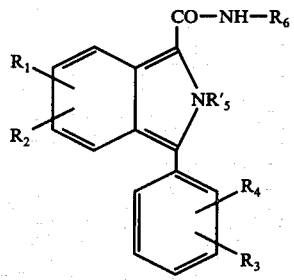

wherein $R_1$, $R_2$, $R_3$, $R_4$ and $R_6$ are as previously described and $R'_5$ is alkyl,
with a compound of the formula

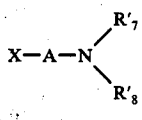

wherein A, X, $R'_7$ and $R'_8$ are as previously described, or (d) to prepare compounds of formula I wherein Z is a group of the formula —$NR_6$—, $R_5$ is alkyl, and $R_7$ and $R_8$, independently, are alkyl, cycloalkyl, cycloalkylalkyl, alkoxyalkyl, aryl or aralkyl, or $R_7$ and $R_8$, when taken together, are a group of the formula —$(CH_2)_n$—, wherein $n$ is an integer of from 2-7, or —$NR_7R_8$ is a 5-membered or 6-membered saturated heterocyclic group containing oxygen or an additional nitrogen atom substituted with alkyl and A, $R_1$, $R_2$, $R_3$, $R_4$ and $R_6$ are as previously described, reacting a compound of the formula

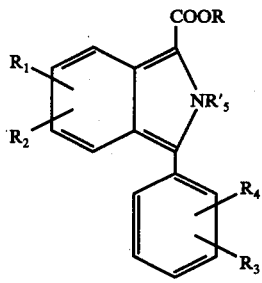

wherein $R_1$, $R_2$, $R_3$, $R_4$ and $R'_5$ are as previously described and R is alkyl,
with a diamine of the formula

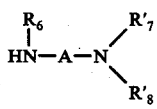

wherein A, $R_6$, $R'_7$ and $R'_8$ are as previously described, or (e) to prepare compounds of formula I wherein Z is the group of the formula —NH—, $R_5$ is hydrogen and $R_7$ and $R_8$, independently, are hydrogen, alkyl, cycloalkyl, cycloalkylalkyl, alkoxyalkyl, aryl or aralkyl, or $R_7$ and $R_8$, when taken together, are a group of the formula —$(CH_2)_n$—, wherein $n$ is an integer of from 2-7, or —$NR_7R_8$ is a 5-membered or 6-membered saturated heterocyclic group containing oxygen or an additional nitrogen substituted with alkyl, with the proviso that at least one of $R_7$ and $R_8$ is other than hydrogen, and A, $R_1$, $R_2$, $R_3$ and $R_4$ are as previously described, reacting a benzodiazepine derivative of the formula

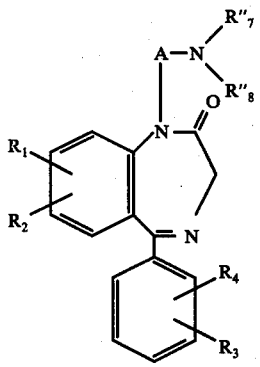

wherein A, $R_1$, $R_2$, $R_3$ and $R_4$ are as previously described and $R''_7$ and $R''_8$, independently, are hydrogen, alkyl, cycloalkyl, cycloalkylalkyl, alkoxyalkyl, aryl or aralkyl, or $R''_7$ and $R''_8$, when taken together, are a group of the formula —$(CH_2)_n$—, wherein $n$ is an integer of from 2-7, or —$NR''_7R''_8$ is a 5-membered or 6-membered saturated heterocyclic group containing oxygen or an additional nitrogen substituted with alkyl, with the proviso that at least one of $R'''_7$ and $R''_8$ is other than hydrogen, with a strong base, or (f) to prepare compounds of formula I wherein $R_7$ is hydrogen and $R_8$ is hydrogen, alkyl, cycloalkyl, cycloalkylalkyl, alkoxyalkyl or aralkyl and A, Z, $R_1$, $R_2$, $R_3$, $R_4$ and $R_5$ are as previously described, reductively aminating a compound of the formula

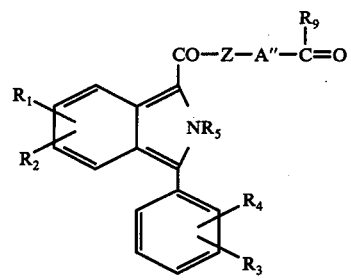

wherein $R_9$ is hydrogen or alkyl and A" is alkylene of 1-7 carbon atoms, with the proviso that A" and $R_9$, when taken together contain at most 7 carbon atoms, and Z, $R_1$, $R_2$, $R_3$, $R_4$ and $R_5$ are as previously described, with an amine of formula III wherein $R_7$ is hydrogen and $R_8$ is hydrogen, alkyl, cycloalkyl, cycloalkylalkyl, alkoxyalkyl or aralkyl, or (g) to prepare compounds of formula I wherein $R_7$ and $R_8$, independently, are hydrogen, alkyl, cycloalkyl, cycloalkylalkyl, alkoxyalkyl or aralkyl, with the proviso that at least one of $R_7$ and $R_8$ is other than hydrogen, and A, Z, $R_1$, $R_2$, $R_3$, $R_4$ and $R_5$ are as previously described, appropriately monosubstituting or disubstituting the nitrogen atom of the group —$NHR'''_7$ in a compound of the formula

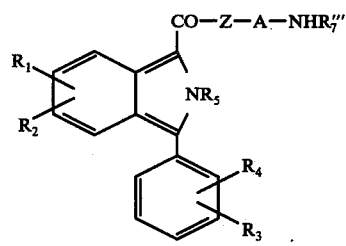

wherein A, Z, $R_1$, $R_2$, $R_3$, $R_4$ and $R_5$ are as previously described, and $R'''_7$ is hydrogen, alkyl, cycloalkyl, cycloalkylalkyl, alkoxyalkyl or aralkyl, or (h) to prepare compounds of formula I wherein $R_7$ is hydrogen and A, Z, $R_1$, $R_2$, $R_3$, $R_4$, $R_5$, $R_6$ and $R_8$ are as previously described, cleaving the protecting group in a compound of the formula

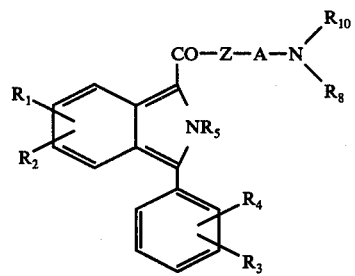

wherein A, Z, R$_1$, R$_2$, R$_3$, R$_4$, R$_5$, R$_6$ and R$_8$ are as previously described, and R$_{10}$ is a protecting group, or (i) to prepare compounds of formula I, with the proviso that when R$_5$ is hydrogen, then Z is oxygen or the group of formula —NH— and R$_7$ and R$_8$ are hydrogen, and A, Z, R$_1$, R$_2$, R$_3$, R$_4$ and R$_5$ are as previously described, reducing a compound of the formula

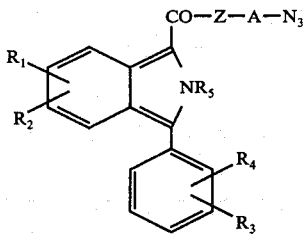

XII wherein A, Z, R$_1$, R$_2$, R$_4$ and R$_5$ are as previously described, with the proviso that when R$_5$ is hydrogen, then Z is oxygen or the group of the formula —NH—, or (j) to prepare compounds of formula I wherein Z is oxygen, R$_5$ is hydrogen and R$_7$ and R$_8$, independently, are hydrogen, alkyl, cycloalkyl, cycloalkylalkyl, alkoxyalkyl, aryl or aralkyl, or R$_7$ and R$_8$, when taken together, is a group of the formula —(CH$_2$)$_{\bar{n}}$, wherein $n$ is an integer of from 2–7, or —NR$_7$R$_8$ is a 5-membered or 6-membered saturated heterocyclic group containing oxygen or an additional nitrogen atom substituted with alkyl, with the proviso that at least one of R$_7$ and R$_8$ is other than hydrogen, and A, R$_1$, R$_2$, R$_3$ and R$_4$ are as previously described, reacting a benzodiazepine derivative of the formula

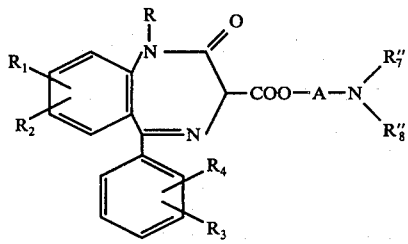

XIII wherein A, R, R$_1$, R$_2$, R$_3$, R$_4$, R″$_7$ and R″$_8$ are as previously described,
with a strong base, and (k) if desired, converting a compound of formula I obtained into a pharmaceutically acceptable acid addition salt.

The reaction of a compound of formula II with an amine of formula III is carried out according to known methods, conveniently in the presence of an excess of the amine of formula III. For instance, the reaction is carried out in an inert organic solvent, for example, an aromatic hydrocarbon, such as, benzene or toluene, a chlorinated hydrocarbon, such as, methylene chloride, an ether, such as, diethyl ether, and the like. The reaction is preferably carried out in the presence of an acid binding agent. Bases such as potassium carbonate, sodium carbonate and the like are suitable acid binding agents. The temperature and pressure of the reaction are not critical. The reaction is preferably carried out at a temperature in the range of from about 0° C. to the reflux temperature of the reaction mixture. If a gaseous amine of formula III is utilized, the reaction is conveniently carried out under pressure, for example, under a pressure of 1–100 atmospheres. If, on the other hand, a liquid amine is used, the reaction is conveniently carried out under normal pressure. When the reaction is carried out under normal pressure, reflux conditions are preferred.

The reductive amination of a compound of formula IV with an amine of formula III, wherein R$_7$ is hydrogen and R$_8$ is hydrogen or alkyl, is carried out according to various known methods by reacting a compound of formula IV with said amine of formula III in the presence of a suitable reducing agent. Thus, the reductive amination can be carried out, for example, in the presence of catalytically activated hydrogen, preferably in the presence of Raney-nickel, in an organic solvent, such as, an alcohol, preferably ethanol, at a temperature in the range of from room temperature to about 100° C. and at a pressure of 1–100 atmospheres. Moreover, formic acid, sodium cyanoborohydride, sodium borohydride and the borane/dimethylamine complex can be used as the reducing agent. The choice of the solvent and usual reductive amination conditions, for example, the temperature, depend primarily on the reducing agent utilized. Thus, the reductive amination in the presence of sodium cyanoborohydride is preferably carried out in methanol at room temperature at a pH between 6 and 8 and the reductive amination in the presence of the borane/dimethylamine complex is preferably carried out in glacial acetic acid at a temperature between room temperature and the reflux temperature of the mixture. If formic acid is used as the reducing agent, then it preferably and simultaneously serves as the solvent. When formic acid is used as the reducing agent, the reductive amination is preferably carried out at a temperature in the range of from about 100° C. to about 150° C. The reductive amination using sodium borohydride as the reducing agent is carried out in a suitable organic solvent, such as, an alcohol, preferably at room temperature.

The reaction of a compound of formula V with a compound of formula VI is also carried out according to known methods, conveniently in the presence of an excess of the compound of formula VI. The reaction is carried out in an inert organic solvent, for example, dimethylformamide, dimethylsulfoxide, diethyleneglycol dimethyl ether, hexametylphosphoric acid triamide and the like, dimethylformamide being the preferred solvent. The reaction is preferably carried out at a temperature in the range of from about 0° C. to about 100° C. preferably at a temperature in the range of from about 40° C. to about 70° C. The reaction is preferably carried out after the prior conversion of a compound of formula V into a corresponding N-(alkali metal) derivative. The N-(alkali metal) derivatives, of which the N-sodium derivatives are preferred, are prepared according to known methods using agents which are customarily used for this purpose, for example, sodium hydride, sodium ethylate and the like.

The reaction of a compound of formula VII with a diamine of formula VIII is carried out according to known methods in the presence of a base in an inert solvent, for example, dimethylformamide, dimethylsulfoxide, hexamethylphosphoric acid triamide, dimethoxyethane and the like, dimethylformamide is the preferred solvent. The reaction is carried out under an atmosphere of inert gas, preferably nitrogen or argon, at a temperature in the range of from about 50° C. to about 150° C., preferably at a temperature in the range of from about 100° C. to about 130° C. Sodium hydride, sodium, butyllithium and the like are exemplary of suitable bases for use in this reaction.

The reaction of a benzodiazepine derivative of formula IX with a strong base is carried out according to known methods in the presence of an inert organic solvent, for example, dimethylformamide, dimethylsulfoxide, hexamethylphosphoric acid triamide and the like, dimethylformamide is the preferred solvent. The reaction is carried out under an atmosphere of inert gas, preferably nitrogen, at a temperature in the range of from about −20° C. to about 100° C., preferably at a temperature in the range of from about 50° C. to about 80° C. Sodium hydride, potassium tert.-butylate and the like are exemplary of suitable strong bases for use in this reaction.

The reductive amination of a compound of formula X is carried out according to known methods by reacting a compound of formula X with an amine of formula III wherein $R_7$ is hydrogen and $R_8$ is hydrogen, alkyl, cycloalkylalkyl, alkoxyalkyl or aralkyl in the presence of a suitable reducing agent. Thus, the reductive amination can be carried out, for example, in the presence of catalytically activated hydrogen, preferably in the presence of Raney-nickel, in an organic solvent, for example, an alcohol, preferably ethanol, at a temperature in the range of from about room temperature to about 100° C., and at a pressure of 1–100 atmospheres. Moreover, formic acid, sodium cyanoborohydride, sodium borohydride as well as the borane/dimethylamine complex are exemplary of suitable reducing agents. The choice of the solvent, as well as of the usual reductive amination conditions, for example, temperature, primarily depend on the reducing agent utilized. The reductive amination in the presence of sodium cyanoborohydride is preferably carried out, for example, in methanol at room temperature at a pH between 6 and 8 and the reductive amination with the borane/dimethylamine complex is preferably carried out, for example, in glacial acetic acid at a temperature in the range of from about room temperature to about the reflux temperature of the mixture. If formic acid is used as the reduction agent, then it preferably and simultaneously serves as the solvent, the preferred temperature range lies between about 100° C. and 150° C. The reductive amination in the presence of sodium borohydride is preferably carried out in a suitable organic solvent, such as, an alcohol, preferably at room temperature.

The N-substitution of a compound of formula Ia is carried out according to known methods, for example, by reacting a compound of formula Ia with a suitable alkylating, cycloalkylating, cycloalkylalkylating, alkoxyalkylating or aralkylating agent in the presence of an acid binding agent, such as, sodium carbonate, potassium carbonate and the like in an organic solvent, for example, a tert.alkanol, such as, tert.butanol, a hydrocarbon, such as benzene or toluene, an ether, such as diethyl ether, dioxane or tetrahydrofuran, dimethylformamide or the like. An excess of an amine of formula Ia can be utilized and can thereby also serve as the acid binding agent. The reaction is conveniently carried out at a temperature in the range of from about 0° C. to about 50° C., preferably at room temperature. Suitable agents for the N-substitution of compounds of formula Ia are compounds of the formula $R_{11}X$ wherein $R_{11}$ is alkyl, cycloalkyl, cycloalkylalkyl, alkoxyalkyl or aralkyl and X as previously described.

Compounds of formula Ia can also be converted into corresponding compounds of formula I wherein $R_7$ and $R_8$, independently, are hydrogen, alkyl, cycloalkyl, cycloalkylalkyl or aralkyl, with the proviso that at least one of $R_7$ and $R_8$ is other than hydrogen, by reacting a compound of formula Ia with an appropriate aldehyde or ketone in the presence of either formic acid or catalytically activated hydrogen.

The cleavage of the protecting group in a compound of formula XI is carried out, depending on the protecting group present, according to various known methods. If the protecting group is acyl or carbalkoxy, then the cleavage is carried out under conditions which are customary for acid or alkaline hydrolysis, for example, in the presence of an ethanolic solution of hydrochloric acid, sodium hydroxide or potassium hydroxide at a temperature in the range of from about 50° C. to the reflux temperature of the mixture. The cleavage of the carbobenzoxy can be carried out, for example, with hydrobromic acid in glacial acetic acid or by catalytic hydrogenation. The benzyl group is preferably cleaved hydrogenolytically.

The reduction of a compound of formula XII can be carried out in a known manner using a variety of reducing agents. Triphenylphosphine, hydrazine in the presence of palladium/carbon, zinc dust in dimethylformamide, aluminum amalgam in moist ether, sodium sulfide, ammonium sulfide, hydrogen in the presence of palladium/carbon or Raney-nickel at atmospheric pressure and the like are exemplary of suitable reducing agents for this purpose. The choice of the solvent as well as of the usual reduction conditions, for example, temperature, primarily depend on the reducing agent utilized. In general, however, the reduction is carried out at a temperature in the range of from room temperature to the reflux temperature of the mixture.

The reaction of a benzodiazepine derivative of formula XIII with a strong base is carried out in a known manner in the presence of an inert organic solvent, for example, dimethylformamide, dimethylsulfoxide and the like, dimethylformamide being the preferred solvent. The reaction is carried out under an atmosphere of inert gas, preferably nitrogen, at a temperature in the range of from about −20° C. to about 100° C., preferably at a temperature in the range of from about 50° C. to about 80° C. Sodium borohydride or the like is exemplary as suitable strong bases for use in this reaction.

The compounds of formula I are basic and can be converted into pharmaceutically acceptable acid addition salts. Exemplary of such salts are those formed with organic acids, such as, oxalic acid, citric acid, acetic acid, lactic acid, maleic acid, fumaric acid, ascorbic acid, salicyclic acid, tartaric acid, or the like, and with inorganic acids, such as, hydrochloric acid, hydrobromic acid, sulfuric acid, phosphoric acid, or the like.

Formula Schemes I, II and III set forth hereinafter illustrate the preparation of starting materials used in the described processes. In these Formula Schemes, A, X, R, $R_1$, $R_2$, $R_3$, $R_4$, $R_5$, $R'_5$, $R_6$, $R_7$ and $R'_8$ are as herein described, $R'_6$ is hydrogen or alkyl, with the proviso that $R'_6$ is hydrogen where $R_5$ is hydrogen, $R''_6$ is alkyl and D is 2-tetrahydropyranyl or 1-ethoxyethyl.

Formula Scheme I
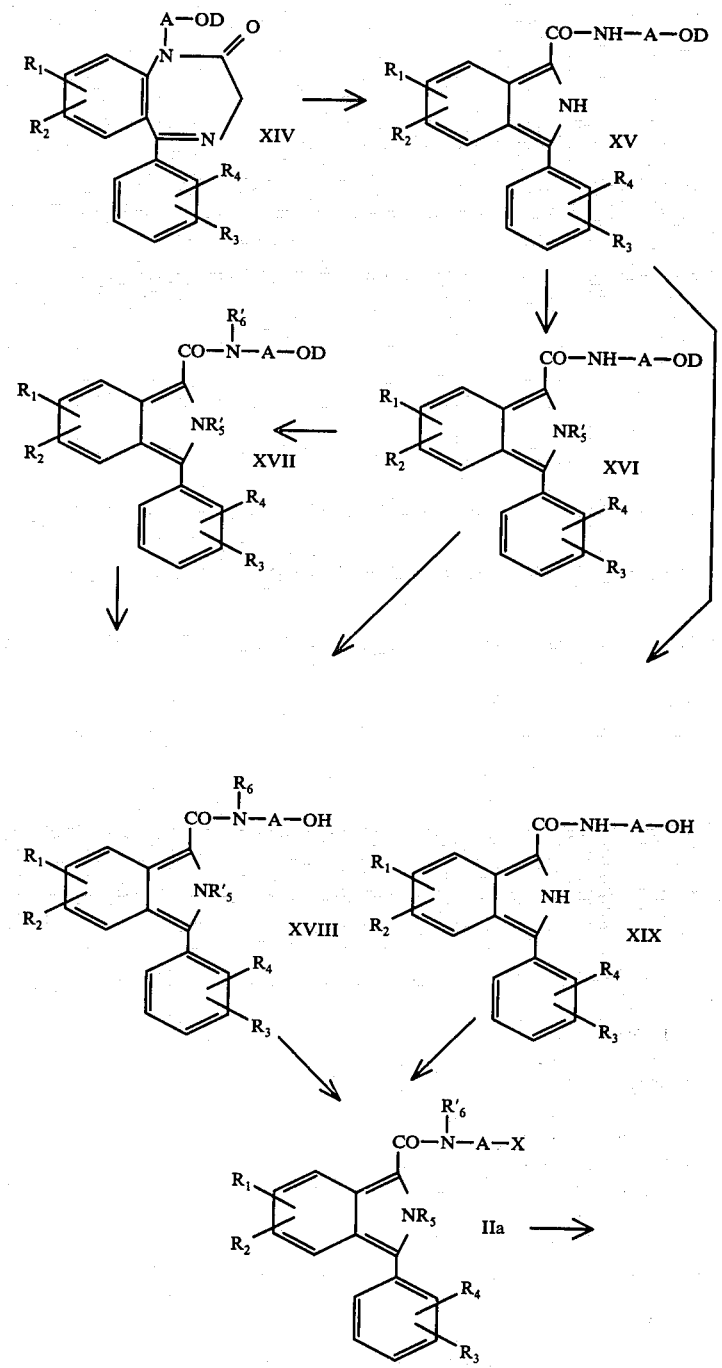

Formula Scheme I
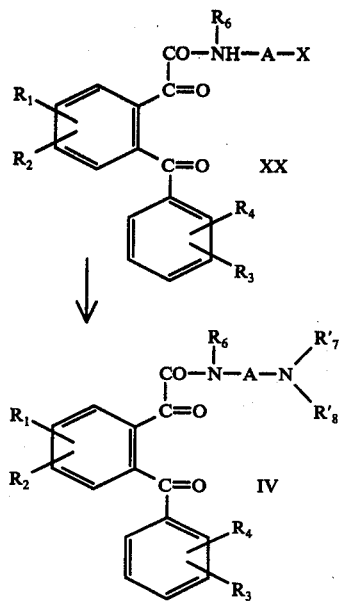
Formula Scheme II
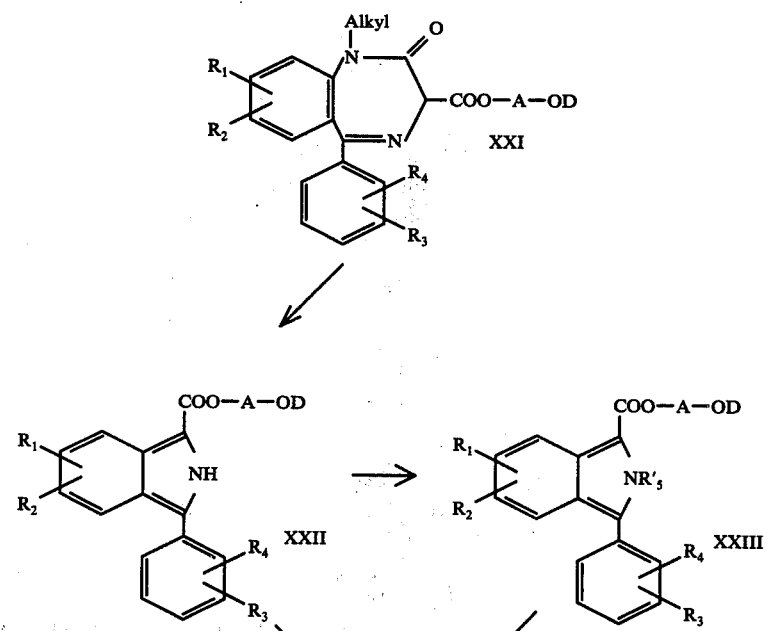

-continued

Formula Scheme II

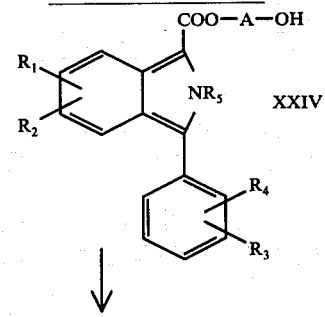

XXIV

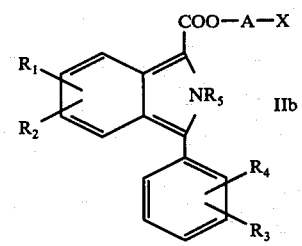

IIb

Formula Scheme III

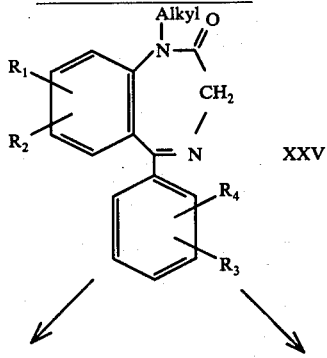

XXV

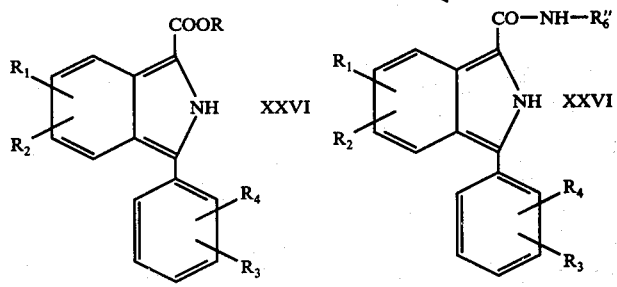

XXVI          XXVI

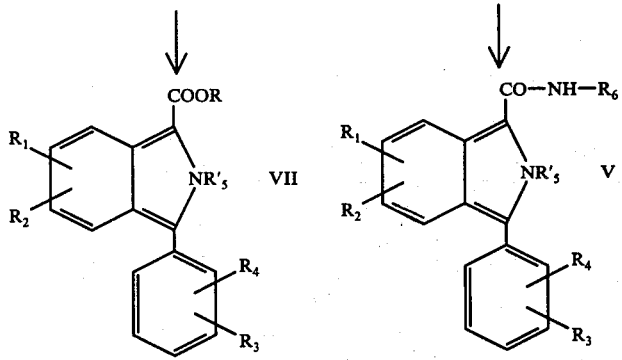

VII          V

With reference to Formula Scheme I, in the first step a compound of formula XIV is reacted in a known manner in an inert organic solvent, for example, dimethylformamide, dimethylsulfoxide, hexamethylphosphoric acid triamide and the like, with a strong base such as sodium hydride, potassium tert.-butylate and the like. The reaction is preferably carried out under an atmosphere of inert gas, preferably nitrogen, at a temperature in the range of from about −20° C. to about 100° C., preferably at a temperature in the range of from about 50° C. to about 80° C.

Compounds of formula XVI can be obtained in a known manner by reacting compounds of formula XV with an alkylating agent, for example, methyl tosylate or dimethylsulfate. The reaction is conveniently carried out in the presence of an inert organic solvent such as dimethylformamide, dimethylsulfoxide, hexamethylphosphoric acid triamide and the like, under normal pressure and at room temperature. A compound of formula XV is preferably converted into a corresponding 2-(alkali metal) derivative prior to the reaction. The 2-(alkali metal) derivatives, of which the 2-sodium derivatives are preferred, are prepared according to known methods using agents which are customarily used for this purpose, for example, sodium hydride, sodium methylate and the like.

Compounds of formula XVII can be obtained according to known methods by reacting compounds of formula XVI with a suitable alkylating agent, for example, an alkyl iodide, dialkylsulfate and the like. The reaction is conveniently carried out in the presence of an inert organic solvent, for example, dimethylformamide, dimethylsulfoxide, hexamethylphosphoric acid triamide and the like, under normal pressure and at a temperature in the range of from room temperature to about 80° C. Prior to the reaction, the compounds of formula XVI are converted into the corresponding N-(alkali metal) derivatives using agents which are customarily used for this purpose, such as, potassium tert.butylate, sodium hydride and the like.

Compounds of formulas XV, XVI and XVII can readily be converted into the corresponding compounds of formulas XVIII or XIX by means of customary hydrolysis procedures at a pH below 7. The compounds to be hydrolyzed can be dissolved in an aqueous medium, in an aqueous lower alkanol, such as, aqueous methanol or aqueous dioxane. Then, the acid agent can be introduced by any suitable method, such as, addition to the resulting medium and the compound to be hydrolyzed. The acid agent can be a mineral acid, such as, hydrochloric acid, aqueous hydrobromic acid or an organic acid, such as, p-toluenesulfonic acid, and the like. By heating the thus-obtained mixture to a temperature in the range of from about 40° C. to about 100° C., preferably to the reflux temperature, the conversion of compounds of formulas XV, XVI and XVII into the corresponding compounds of formula XVIII or XIX can be carried out in a convenient manner.

Compounds of formulas XVIII and XIX can be converted into compounds of formula IIa in a known manner. The conversion is carried out by reacting a compound of formula XVII or XIX with an agent which is capable of replacing the terminal hydroxy group by a leaving atom or group. This reaction is advantageously carried out in the presence of a base, such as, pyridine, triethylamine and the like, in an inert organic solvent, for example, an aromatic hydrocarbon, such as, benzene or toluene, a chlorinated hydrocarbon, such as, methylene chloride, an ether, such as, diethyl ether, and the like. Alternatively, the base used can also serve as the solvent. Suitable agents for the introducton of a leaving atom or a group are thionyl chloride, phosphorus pentachloride, phosphorus tribromide, phosphorus triiodide, p-toluenesulfonyl chloride, methanesulfonyl chloride and the like. The temperature at which the reaction is carried out depends on the agent utilized. Thus, when a sulfonyl chloride is used, the reaction is conveniently carried out at a temperature in the range of from about −10° C. to about room temperature, but if a halogenating agent is used, then the reaction is carried out at a temperature in the range of from about −10° C. to about 100° C., preferably at a temperature in the range of from about room temperature to about 60° C. In a further embodiment, a chlorine atom can also be introduced by reacting a compound of formula XVIII or XIX with triphenylphosphine in carbon tetrachloride, conveniently in the presence of an inert organic solvent, such as, dioxane, at a temperaure in the range of from about room temperature to the reflux temperature of the reaction mixture.

The compounds of formula IIa can be oxidized to the compounds of formula XX in a known manner using a mild oxidizing agent, for example, a ceric salt, such as, ceric ammonium nitrate, ceric nitrate or ceric sulfate, manganese dioxide or oxygen in a suitable slvent such as glacial acetic acid and the like at a temperature in the range of from about 0° C. and the reflux temperature of the mixture, preferably at the reflux temperature.

The reaction of a compound of formula XX with an amine of formula III to give a compound of formula IV is carried out according to known methods, conveniently in the presence of an excess of the amine of formula III. The reaction is carried out in an inert organic solvent, for example, an aromatic hydrocarbon, such as, benzene or toluene, a chlorinated hydrocarbon, such as, methylene chloride, an ether, such as, diethyle ether, and the like. The reaction is preferably carried out in the presence of an acid binding agent. Bases such as potassium carbonate, sodium carbonate and the like are suitable for use in this reaction. The temperature and pressure are not critical. It is preferred to carry out this reaction at a temperature in the range of from about 0° C. to the reflux temperature of the reaction mixture. If a gaseous amine of formula III is utilized, the reaction is conveniently carried out under pressure, for example, under a pressure of 1–100 atmospheres. If, on the other hand, a liquid amine is utilized, the reaction is conveniently carried out under normal pressure. When the reaction is carried out under normal pressure, reflux conditions are preferred.

With reference to Formula Scheme II, in the first step a compound of formula XXI is reacted according to known methods with a strong base, for example, sodium hydride and the like, in an inert organic solvent, for example, dimethylformamide, dimethylsulfoxide and the like. The reaction is preferably carried out under an atmosphere of nitrogen at a temperature in the range of from about −20° C. to about 100° C., preferably at about 50° C. to about 80° C.

In the next step, a compound of formula XXII can be alkylated in the 2-position in a known manner using an alkylating agent, such as, methyl tosylate, dimethylsulfate, ethyl tosylate, diethylsulfate, and the like. The alkylation is conveniently carried out in an inert organic solvent such as dimethylformamide, dimethylsulfoxide, hexamethylphosphoric acid triamide and the like, at atmospheric pressure and room temperature. A compound of formula XXII is converted into a corresponding 2-(alkali metal) derivative prior to the alkylation. The 2-(alkali metal) derivatives, of which the 2-sodium derivatives are preferred, are prepared according to known methods using agents which are customarily used for this purpose, for example, sodium hydride, sodium ethylate and the like.

Compounds of formulas XXII and XXIII can be hydrolyzed to the corresponding compounds of formula XXIV in a known manner by means of customary hydrolysis procedures at a pH value below 7. The hydrolysis is conveniently carried out in an aqueous medium, for example, an aqueous alkanol, such as, methanol or ethanol, aqueous dioxane and the like with an acid, for example, hydrochloric acid, aqueous hydrobromic acid, p-toluenesulfonic acid and the like at a temperature in the range of from about 40° C. to about 100° C., preferably at the reflux temperature of the mixture.

Compounds of formula XXIV can be converted in a known manner into compounds of formula IIb by reaction with a reagent yielding a leaving atom or group, such as, thionyl chloride, phosphorus pentachloride, phosphorus tribromide, p-toluenesulfonyl chloride, methanesulfonyl chloride and the like. The reaction is conveniently carried out in the presence of a base such as pyridine, triethylamine and the like in an inert organic solvent, for example, an aromatic hydrocarbon, such as, benzene or toluene, a chlorinated hydrocarbon, such as, methylene chloride, an ether, such as, diethyl ether and the like. Alternatively, the base can simultaneously serve as the solvent. The temperature is dependent on the agent used. Thus, when a sulfonyl chloride is used, the reaction is conveniently carried out at a temperature in the range of from about −10° C. to room temperature and, when a halogenating agent is used, the reaction is carried out at a temperature in the range of from about −10° C. to 100° C., preferably at a temperature in the range of from room temperature to about 60° C. According to a further embodiment, a chlorine atom can be introduced by reacting a compound of formula XXIV with triphenylphosphine in carbon tetrachloride, conveniently in the presence of an inert organic solvent at a temperature in the range of from room temperature to the reflux temperature of the reaction mixture.

Compounds of formulas XXVI and XXVII in Formula Scheme III, can be prepared from compounds of formula XXV by reaction with a strong base, for example, sodium hydride, potassium tert.-butylate and the like, in an inert organic solvent, for example, dimethylformamide, dimethylsulfoxide, hexamethylphosphoric acid triamide and the like, if desired in the presence of a carbonic acid ester of the formula $$CO(OR)_2$$

wherein r is as previously described.

The reaction is preferably carried out under an atmosphere of nitrogen at a temperature in the range of about −20° C. to about 100° C., preferably at about 50°–80° C. If the reaction is carried out in the presence of a carbonic acid ester, there is obtained a compound of formula XXVI. On the other hand, if the reaction is carried out in the absence of a carbonic acid ester, there is obtained a corresponding amide, that is, a compound of formula XXVII.

Compounds of formulas VII and V wherein $R_6$ is alkyl, can be prepared in a known manner by reacting compounds of formulas XXVI and XXVII with an alkylating agent, for example, methyl tosylate or dimethylsulfate. The reaction is conveniently carried out in the presence of an inert organic solvent, for example, dimethylformamide dimethylsulfoxide, hexamethylphosphoric acid triamide and the like, at normal pressure and at room temperature. Prior to this reaction, a compound of formula XXVI or XXVII is converted into a corresponding 2-(alkali metal) derivative. The 2-(alkali metal) derivatives, of which the 2-sodium derivatives are preferred, are obtained according to known methods using gents which are customarily used for this purpose, for example, sodium hydride, sodium methylate and the like.

Compounds of formula V can also be prepared from compounds of formula VII by reaction in a known manner with an amine of formula III wherein $R_7$ is hydrogen and $R_8$ is hydrogen or alkyl in the presence of a base, for example, sodium hydride, sodium butyllithium and the like, in an inert organic solvent, for example, dimethylformamide, dimethylsulfoxide, hexamethylphosphoric acid triamide and the like. The reaction is preferably carried out under an atmosphere of nitrogen at a temperature in the range of from about 50° C. to about 150° C., preferably at a temperature in the range of from about 100° C. to about 130° C. Sodium amide can be used in place of ammonia and a base as the reagent for the introduction of the primary amide group.

The benzodiazepine derivatives of formulas XIV and XXI are novel, and can be obtained in analogy to the preparation of similar known derivatives. Thus, the benzodiazepine derivatives of formula XIV can be prepared in a simple manner by the appropriate 1-substitution of a corresponding 1-unsubstituted prior-known benzodiazephine derivative. In a similar manner, the benzodiazepine derivatives of formula XXI can be prepared by re-esterification of a prior-known 3-carboalkoxy-substituted benzodiazepine derivative.

The benzodiazepine derivatives of formula XXV are known or can be prepared in analogy to the preparation of the known derivatives.

The compounds of formula IIa wherein $R'_6$ and $R_5$ each is alkyl, can be prepared by reacting corresponding compounds of formula V with a compound of the formula $$X-A-X$$

wherein A is as previously described, and each X is a leaving atom or group.

The reaction is conveniently carried out in the presence of an inert organic solvent, for example, dimethylformamide, dimethylsulfoxide, hexamethylphosphoric acid triamide, nitromethane, N-methylpyrrolidone and the like, at normal pressure and room temperature. A compound of formula V is converted into a corresponding N-(alkali metal) derivative prior to the reaction. The N-(alkali metal) derivatives, of which the N-sodium derivatives are preferred, are prepared according to known methods utilizing agents which are customarily used for this purpose, for example, sodium hydride, sodium ethylate and the like.

The compounds of formula IV can also be prepared from corresponding compounds of formula I by oxidation in the manner described earlier in connection with the conversion of a compound of formula IIa into a compound of formula XX. The oxidation is carried out utilizing the same oxidizing agents and under the same conditions as for the oxidation of a compound of formula IIa.

Compounds of formulas X and XI can be prepared from benzodiazepine derivatives of the formula

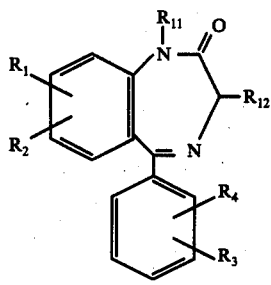

XXVIII wherein $R_{11}$ is a group of the formula

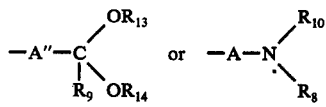

and $R_{12}$ is hydrogen or $R_{11}$ is alkyl and $R_{12}$ is a group of the formula

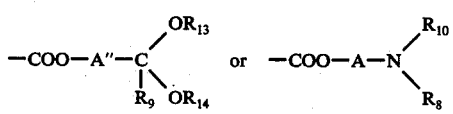

wherein $R_{13}$ and $R_{14}$, independently, are alkyl or $R_{13}$ and $R_{14}$, when taken together, are —$CH_2$—$CH_2$— or —$CH_2$—$CH_2$—$CH_2$— and A, A'', $R_1$, $R_2$, $R_3$, $R_4$, $R_8$, $R_9$ and $R_{10}$ are as previously described,
by reaction in an inert organic solvent, for example, dimethylformamide, dimethylsulfoxide and the like with a strong base, such as, sodium hydride and the like. The reaction is preferably carried out under an atmosphere of nitrogen at a temperature in the range of from about −20° C. to about 100° C., preferably at a temperature in the range of from about 50° C. to about 80° C. The resulting compounds of the formula

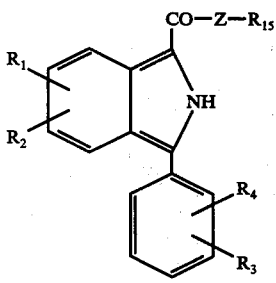

XXIX wherein $R_{15}$ is a group of the formula

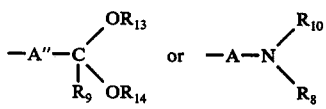

and A, A'', $R_1$, $R_2$, $R_3$, $R_4$, $R_8$, $R_9$, $R_{10}$, $R_{13}$ and $R_{14}$ are as previously described, can, if desired, be alkylated in the 2-position according to known methods. The alkylation is carried out using the same alkylating agents and under the same conditions as described earlier in connection with the 2-alkylation of a compound of formula XV.

It will be appreciated that the compounds of formula XXIX wherein $R_{15}$ is a group of the formula

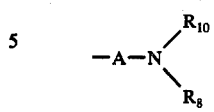

wherein $R_8$ and $R_{10}$ are as previously described, or their 2-alkyl derivatives represent the compounds of formula XI.

For the preparation of compounds of formula X, the compounds of formula XXIX wherein $R_{15}$ is a group of the formula

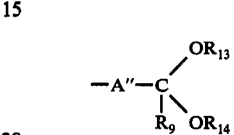

wherein A'', $R_9$, $R_{13}$ and $R_{14}$ are as previously described, or their 2-alkyl derivatives are hydrolyzed in a known manner at a pH below 7, for example, by treatment with an acid, such as, hydrochloric acid, aqueous hydrobromic acid, p-toluenesulfonic acid and the like, in an aqueous medium, such as, an aqueous lower alkanol, such as, methanol or ethanol, aqueous dioxane and the like, at a temperature in the range of from about 0° C. to about 100° C., preferably at the reflux temperature of the mixture.

Compounds of formula XI wherein $R_{10}$ is benzyl, can also be prepared, for example, by reacting a compound of formula II with a compound of the formula

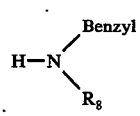

wherein $R_8$ is as previously described.

The reaction can be carried out under the conditions described earlier for the reaction of a compound of formula II with an amine of formula III.

Compounds of formula XII can be prepared from compounds of formula II by treatment with an agent yielding an azide group, for example, alkali metal azide, such as, sodium azide, potassium azide or lithium azide; an alkaline earth metal azide, such as, calcium azide; ammonium azide; and the like. Preferred is sodium azide. The treatment is conveniently carried out in an inert organic solvent, such as dimethylformamide, dimethylsulfoxide, hexamethylphosphoric acid triamide and the like at a temperature in the range of from about 0° C. to about 70° C., preferably at a temperature in the range of from about 30° C. to about 60° C.

The compounds of formulas III, VI, VIII, IX and XIII are known or can be prepared in analogy to the preparation of known compounds.

The starting materials of formulas II, IV, V, VII, X, XI and XII are novel and also form part of the present invention.

The isoindole derivatives provided by the present invention, that is, the compounds of formula I and their pharmaceutically acceptable acid addition salts, can be used as medicaments. They possess, for example, a pronounced anorectic activity and are useful as appetite-suppressants, especially since, in contrast to other appetite-suppressors, they have practically no central-stimulating activity. The anorectic activity is demonstrated by administering the derivative to be tested in four doses of 300 μmol/kg. or less in 5% gum arabic orally to groups each comprising six male rats which are given food ad libitum in the test for 48 hours. Subsequently, 24 and 48 hours after the first administration, the food consumption is determined by weighing the food vessels and compared with the food consumption of untreated control animals (100%). The $ED_{65}$ denotes the dose of the derivative in mg/kg. which reduces the food consumption to 65% of that of the controls. Thus, for example, 5-chloro-3-phenylisoindole-1-carboxylic acid 3-(diethylamino)propyl ester (derivative A) has an $ED_{65}$ of 13.1 mg/kg., 3-(p-chlorophenyl)-isoindole-1-carboxylic acid [2-(diethylamino)ethyl]amide (derivative B) has an $ED_{65}$ of 4.8 mg/kg. and 5-chloro-3-(p-chlorophenyl)isoindole-1-carboxylic acid [2-(diethylamino)ethyl]amide (derivative C) has an $ED_{65}$ of 10.5 mg/kg. The toxicity values ($LD_{50}$) were determined according to standard methods on the mouse and amount to 600 mg/kg for derivative A, 1250 mg/kg for derivative B and 2500 mg/kg. for derivative C.

The isoindole derivatives provided by this invention can be used as medicaments, for example, in the form of pharmaceutical preparations which contain them in association with a compatible pharmaceutical carrier material. This carrier material can be an organic or inorganic inert carrier material suitable for enteral or parenteral administration, such as, for example, water, gelatin, gum arabic, lactose, starch, magnesium stearate, talc, vegetable oils, polyalkyleneglycols, and the like. The pharmaceutical preparations can be made up in a solid form, for example, as tablets, dragees, suppositories or capsules, or in liquid form, for example, as solutions, suspensions or emulsions. The pharmaceutical preparations may be sterilized and/or may contain adjuvants such as preserving, stabilizing, wetting or emulsifying agents, salts for varying the osmotic pressure, or buffers. They can also contain other therapeutically valuable substances.

Expedient pharmaceutical dosage forms contain about 1 to 30 mg. of a compound of formula I. Convenient oral dosage ranges lie at about 0.1 mg/kg per day to about 0.5 mg/kg. per day. The aforementioned range can, however, be increased or decreased depending on individual requirements.

The Examples which follow further illustrate the invention. All temperatures are in degrees Centigrade, unless otherwise stated.

EXAMPLE 1

Preparation of 3-(p-chlorophenyl)isoindole-1-carboxylic acid [2-(diethylamino)ethyl]amide A solution of 11.1 g. of 5-(p-chlorophenyl)-1-[2-(diethylamino)ethyl]-1,3-dihydro-2H-1,4-benzodiazepin-2-one in 100 ml. of dimethylformamide is treated under an atmosphere of argon at room temperature with 0.035 mol. of sodium hydride (1.55 g. of a 55% dispersion in mineral oil). The mixture is first warmed to 60° C. over a period of about 30 minutes, then stirred at this temperature for 1 hour and thereafter at 70° C. for 1 hour. After cooling, 4 ml. of water are added dropwise and the mixture is then poured on to 800 ml. of ice-water. After the addition of 30 g. of sodium chloride, the precipitated product is extracted with methylene chloride. The organic phase is washed with a saturated sodium chloride solution, dried over sodium sulfate and concentrated to dryness. The oily residue obtained crystallizes upon trituration with hexane. Recrystallization from ethyl acetate yields 3-(p-chlorophenyl)isoindole-1-carboxylic acid [2-(diethylamino)ethyl]amide in the form of felt-like greenish crystals having a melting point of 145°-147° C.

The starting material can be prepared as follows:

A suspension of 19.0 g. of 5-(p-chlorophenyl)-1,3-dihydro-2H-1,4-benzodiazepin-2-one in 180 ml. of dimethylformamide is treated under an atmosphere of argon at 0° C. with 11.7 g. of potassium tertiary butylate and the mixture is stirred in an ice-bath for 15 minutes. Then, there is added at 0°-5° C. a solution of 0.14 mol. of diethylaminoethyl chloride in 200 ml. of toluene (freshly prepared from the corresponding hydrochloride and dried over sodium sulfate), the mixture is stirred at room temperature for 30 minutes and finally heated to 100° C. for 30 minutes. After cooling, the toluene is removed by evaporation under reduced pressure and the residual solution poured on to 800 ml. of ice-water. The separated oily product is extracted with methylene chloride and the organic phase washed with a saturated sodium chloride solution, dried over sodium sulfate and concentrated to dryness. The residual oil is chromatographed on 600 g. of aluminum oxide (neutral, Brockmann, activity I) using methylene chloride/ethyl acetate (4:1) for the elution. The homogeneous fractions yield, after crystallization from hexane, 5-(p-chlorophenyl)-1-[2-(diethylamino)ethyl]-1,3-dihydro-2H-benzodiazepin-2-one having a melting point of 51°-54° C.

In a manner analogous to that described above, the following isoindole derivatives can be prepared:

| Benzodiazepine derivative | Isoindole derivative |
| --- | --- |
| 7-Chloro-1-[2-(diethylamino)ethyl]-1,3-dihydro-5-phenyl-2H-1,4-benzodiazepin-2-one; melting point 79° - 81° C. | 5-Chloro-3-phenylisoindole-1-carboxylic acid[2-(diethylamino)ethyl]amide; melting point 173° - 175° C. |
| 7-Chloro-5-(p-chlorophenyl)-1-[2-(diethylamino)ethyl]-1,3-dihydro-2H-1,4-benzodiazepin-2-one; melting point 117° - 118° C. | 5-Chloro-3-(p-chlorophenyl)-isoindole-1-carboxylic acid [2-(diethylamino)ethyl]-amide; melting point 186° - 188° C. |
| 7,9-Dichloro-1-[2-(diethylamino)ethyl]-1,3-dihydro-5-phenyl-2H-1,4-benzodiazepin-2-one [dihydrochloride; melting point 208° - 211° C. (decomposition)]. | 5,7-Dichloro-3-phenylisoindole-1-carboxylic acid[2-(diethylamino)ethyl]amide; melting point 130° - 132° C. |
| 7-Chloro-1-[2-(diethylamino)-ethyl]-5-(o-fluorophenyl)-1,3-dihydro-2H-1,4-benzodiazepin-2-one [dihydrochloride; melting point 190° - 220° C. (decomposition)]. | 5-Chloro-3-(o-fluorophenyl)-isoindole-1-carboxylic acid [2-(diethylamino)ethyl]-amide hydrochloride; melting point 178° - 180° C. (decomposition). |
| 7-Chloro-1-[3-(diethylamino)-propyl]-1,3-dihydro-5-phenyl-2H-1,4-benzodiazepin-2-one; melting point 89° - 91° C. | 5-Chloro-3-phenylisoindole-1-carboxylic acid [3-(diethylamino)propyl]amide; melting point 133° - 135° C. |
| 7-Chloro-1,3-dihydro-1-[3-(dimethylamino)- | 5-Chloro-3-phenylisoindole-1-carboxylic |

-continued

| Benzodiazepine derivative | Isoindole derivative |
|---|---|
| propyl]-5-phenyl-2H-1,4-benzodiazepin-2-one; melting point 90° – 92° C. | acid [3-(dimethylamino)propyl]amide; melting point 167° – 169° C. |
| 7-Chloro-1,3-dihydro-1-(2-morpholinoethyl)-5-phenyl-2H-1,4-benzodiazepin-2-one; melting point 144° – 146° C. | 5-Chloro-3-phenylisoindole-1-carboxylic acid (2-morpholinoethyl)amide; melting point 178° – 180° C. |
| 7-Chloro-1,3-dihydro-5-phenyl-1-[2-(1-pyrrolidinyl)ethyl]-2H-1,4-benzodiazepin-2-one; melting point 106° – 107° C. | 5-Chloro-3-phenylisoindole-1-carboxylic acid [2-(1-pyrrolidinyl)ethyl]amide p-toluenesulfonate; melting point 131° – 134° C. (decomposition). |
| 7-Chloro-1,3-dihydro-5-phenyl-1-(2-piperidinoethyl)-2H-1,4-benzodiazepin-2-one; melting point 90° – 92° C. | 5-Chloro-3-phenylisoindole-1-carboxylic acid (2-piperidinoethyl)amide; melting point 180° – 181° C. |
| 7-Chloro-1,3-dihydro-1-[3-(4-methyl-1-piperazinyl)propyl]-5-phenyl-2H-1,4-benzodiazepin-2-one; melting point 122° – 124° C. | 5-Chloro-3-phenylisoindole-1-carboxylic acid[3-(4-methyl-1-piperazinyl)propyl]amide; melting point 126° – 128° C. |

EXAMPLE 2

Preparation of 5-chloro-2-methyl-3phenylisoindole-1-carboxylic acid [2-(diethylamino)ethyl]methylamide cyclohexanesulfamate A suspension of 15.0 g. of 5-chloro-2-methyl-3-phenylisoindole-1-carboxylic acid methylamide in 190 ml. of dimethylformamide is treated under an atmosphere of argon with 8.25 g. of potassium tertiary butylate and the mixture is stirred in an ice-bath for 15 minutes. At 0°–5° C., there is then added a solution of 0.1 mol. of diethylaminoethyl chloride in 150 ml. of toluene (freshly prepared from the corresponding hydrochloride and dried over sodium sulfate), the mixture is stirred first at room temperature for 30 minutes and then at 100° C. for 30 minutes. After cooling, the toluene is removed by distillation under reduced pressure and the residual solution poured on to 600 ml. of ice-water. The separated thick oil is extracted with methylene chloride, and the extract washed with a saturated sodium chloride solution, dried over sodium sulfate and concentrated to dryness. The residue obtained is dissolved in 60 ml. of isopropanol and treated with 9.0 g. of N-cyclohexylsulfamic acid. 200 ml. of diethyl ether are gradually added and the mixture is left to stand at room temperature for 1 hour. The almost colorless salt which crystallizes out is removed by filtration, washed with a small amount of diethyl ether and dried in a desiccator. Recrystallization from acetone yields 5-chloro-2-methyl-3-phenylisoindole-1-carboxylic acid [2-(diethylamino)ethyl]methylamide cyclohexanesulfamate having a melting point of 166°–168° C. (decomposition).

EXAMPLE 3

Preparation of 5-chloro-2-methyl-3-phenylisoindole-1-carboxylic acid[2-(diethylamino)ethyl]amide hydrochloride A solution of 7.45 g. of methylamine in 120 ml. of methanol is treated with 12 ml. of 6.65-N methanolic hydrochloric acid. Thereafter, there are successively added under an atmosphere of argon at 20°–25° C. 17.0 g. of o-benzoyl-p-chlorophenylglyoxylic acid [2-(diethylamino)ethyl]amide hydrochloride and 1.6 g. of sodium cyanoborohydride and the mixture is stirred at room temperature for an additional 2 hours. The mixture is made acidic with concentrated hydrochloric acid while cooling with ice, stirred at room temperature for an additional 0.5 hour and evaporated to dryness under reduced pressure. The residue is made alkaline with 2-N ammonium hydroxide with the addition of ice and extracted with diethyl ether. After drying over sodium sulfate, the extract is concentrated to dryness and the oily residue triturated with hexane to crystallize the product. The product is removed by filtration, dissolved in 30 ml. of methanol and the solution treated with excess ethereal hydrochloric acid. After dilution with diethyl ether to a ten-fold volume, the hydrochloride which crystallizes out is removed by filtration and washed with diethyl ether. Recrystallization from methanol/diethyl ether yields 5-chloro-2-methyl-3-phenylisoindole-1-carboxylic acid [2-(diethylamino)ethyl]amide hydrochloride in the form of almost colorless crystals having a melting point of 211°–214° C. (decomposition).

The starting material can be prepared as follows:

86.4 G. of ceric ammonium nitrate are dissolved in 150 ml. of water and 150 ml. of glacial acetic acid. 22.2 G. of 5-chloro-3-phenylisoindole-1-carboxylic acid [2-(diethylamino)ethyl]amide are added and the mixture is stirred at 80° C. for 20 minutes, the color of the solution obtained changing from orange to light yellow. After cooling, 750 ml. of ice-water are added and the separated oil is extracted with methylene chloride. The extract is washed with 2-N ammonium hydroxide and a saturated sodium chloride solution, dried over sodium sulfate and evaporated. The oily residue is dissolved in diethyl ether and treated with excess ethereal hydrochloric acid. The precipitated hydrochloride is removed by filtration, washed with diethyl ether and dried over phosphorus pentoxide in a desiccator. After recrystallization from methylene chloride/diethyl ether, there is obtained p-benzoyl-p-chlorophenylglyoxylic acid [2-(diethylamino)ethyl]amide hydrochloride in the form of almost colorless crystals having a melting point of 161°–164° C. (decomposition).

EXAMPLE 4

Preparation of 2-ethyl-5-chloro-3-phenylisoindole-1-carboxylic acid[2-(diethylamino)ethyl]amide hydrochloride In an analogous manner to that described in Example 3, from 17.0 g. of o-benzoyl-p-chlorophenylglyoxylic acid [2-(diethylamino)ethyl]amide hydrochloride, 10.8 g. of ethylamine and 1.6 g. of sodium cyanoborohydride there is obtained a solid crude product which, after recrystallization from ethanol/diethyl ether, yields 2-ethyl-5-chloro-3-phenylisoinodole-1-carboxylic acid [2-(diethylamino)ethyl]amide hydrochloride having a melting point of 217°–219° C. (decomposition).

EXAMPLE 5

Preparation of 5-chloro-3-phenylisoindole-1-carboxylic acid[2-(diethylamino)ethyl]methylamide hydrochloride In accordance with the procedure described in Example 3, 16.0 g. of o-benzoyl-p-chlorophenylglyoxylic acid [2-(diethylamino)ethyl]methylamide are reacted with 4.1 g. of ammonia and 1.6 g. of sodium cyanoborohydride. The ether extract containing the free base is concentrated to about 300 ml. and treated with ethereal hydrochloric acid. The precipitated hydrochloride is recrystallized from ethanol, and there is obtained 5-chloro-3-phenylisoindole-1-carboxylic acid [2-(diethylamino)ethyl]methylamide hydrochloride in the form of felt-like greenish crystals having a melting point of 208°–210° C. (decomposition).

The starting material can be prepared as follows:

A solution of 34.6 g. of 5-chloro-2-methyl-3-phenylisoindole-1-carboxylic acid[2-(diethylamino)ethyl]-methylamide cyclohexanesulfamate in 400 ml. of water is treated with excess 2-N ammonium hydroxide. The liberated base is extracted with methylene chloride and the extract evaporated to dryness. To the obtained residue, there is added a solution of 86.4 g. of ceric ammonium nitrate in 150 ml. of water and 150 ml. of glacial acetic acid. The mixture is stirred at 80° C. for 20 minutes, the color of the solution obtained changing from orange to light yellow. After cooling, 750 ml. of ice-water are added and the separated oil is extracted with methylene chloride. The organic phase is washed with 2-N ammonium hydroxide and a saturated sodium chloride solution, dried over sodium sulfate and concentrated to dryness. o-benzoyl-p-chlorophenylglyoxylic acid[2-(diethylamino)ethyl]methylamide is obtained as an oil which can be used in the process without further purification. With 2 mols of N-cyclohexylsulfamic acid, the base forms an addition compound which melts at 136°–138° C. (decomposition) after crystallization from isopropanol/diethyl ether.

EXAMPLE 6

Preparation of 5-chloro-2-methyl-3-phenylisoindole-1-carboxylic acid[2-(diethylamino)ethyl]amide hydrochloride In accordance with the procedure described in Example 2, 2.85 g. of 5-chloro-2-methyl-3-phenylisoindole-1-carboxylic acid amide are reacted with 0.02 mol. of diethylaminoethyl chloride. The methylene chloride extract containing the free base is concentrated to dryness and the pasty residue chromatographed on 300 g. of aluminum oxide (neutral, Brockmann, activity I) using methylene chloride/ethyl acetate (4:1) for the elution. The homogeneous fractions are combined and evaporated. The residual solid residue is dissolved in 10 ml. of acetone and treated with excess ethereal hydrochloric acid. The hydrochloride which crystallizes out is removed by filtration and washed with diethyl ether, whereby there is obtained 5-chloro-2-methyl-3-phenylisoindole-1-carboxylic acid[2-(diethylamino)ethyl]amide hydrochloride having a melting point of 211°–214° C. (decomposition).

The starting material can be prepared as follows:

A solution of 28.5 g. of 7-chloro-1,3-dihydro-1-methyl-5-phenyl-2H-1,4-benzodiazepin-2-one in 400 ml. of dimethylformamide is treated under an atmosphere of argon at −10° C. with 0.25 mol. of sodium hydride (11.0 g. of a 55% dispersion in mineral oil) and the mixture is stirred at the same temperature for 15 minutes. The suspension is then treated at −10° C. to −5° C. with a solution of 35.5 g. of diethylcarbonate in 50 ml. of dimethylformamide. The mixture is stirred at 20° C. for 1 hour and at 60° C. for an additional 4 hours. Then, the mixture is poured on to a mixture of 100 g. of sodium chloride and 2.5 kg. of ice. The precipitate is removed by filtration, washed with water and dissolved in methylene chloride. The organic solution is washed with a saturated aqueous sodium chloride solution, dried over sodium sulfate and concentrated to dryness. The crystalline residue is heated to reflux with 500 ml. of ethanol for 10 minutes and then cooled in an ice-bath. After filtration and washing with ethanol and diethyl ether, there is obtained 5-chloro-3-phenylisoindole-1-carboxylic acid ethyl ester in the form of greenish crystals having a melting point of 208°–210° C. (decomposition). Recrystallization from acetonitrile does not increase the melting point.

A suspension of 15 g. of 5-chloro-3-phenylisoindole-1-carboxylic acid ethyl ester in 150 ml. of dimethylsulfoxide is treated under an atmosphere of argon at 15°–20° C. with 13.8 g. of finely ground dry potassium carbonate and 14 ml. of methyl iodide, the mixture is stirred intensively at room temperature for 1 hour and then poured on to 750 ml. of ice-water. After the addition of 35 g. of sodium chloride, the precipitated product is removed by filtration, washed with water and dissolved in methylene chloride. The organic phase is dried over sodium sulfate and evaporated. The residue crystallizes upon trituration with hexane. Recrystallization from ethanol yields 5-chloro-2-methyl-3-phenylisoindole-1-carboxylic acid ethyl ester in the form of almost colorless crystals having a melting point of 94°–96° C.

A solution of 12.4 g. of 5-chloro-2-methyl-3-phenylisoindole-1-carboxylic acid ethyl ester in 70 ml. of dimethylformamide is treated under an atmosphere of argon at room temperature with 0.1 mol. of sodium amide (8.0 g. of a 50% suspension in toluene) and then stirred at 100° C. for 2 hours. After cooling, the mixture is poured on to 400 ml. of ice-water and the precipitate is removed by filtration, washed with water and dissolved in methylene chloride. The organic solution is washed with water, dried over sodium sulfate and concentrated to dryness. The residue is dissolved in chloroform and chromatographed on 800 g. of silica gel using chloroform/n-heptane/ethanol (10:10:1) for the elution. The uniform fractions are combined and evaporated. After recrystallization from acetonitrile, there is obtained 5-chloro-2-methyl-3-phenylisoindole-1-carboxylic acid amide in the form of yellowish crystals having a melting point of 241°–244° C. (decomposition).

EXAMPLE 7

Preparation of 5-chloro-2-methyl-3-phenylisoindole-1-carboxylic acid [2-(diethylamino)ethyl]amide hydrochloride A solution of 2.3 g. of 2-diethylaminoethylamine in 25 ml. of dimethylformamide is treated under an atmosphere of argon at 5°–10° C. with 0.02 mol. of butyllithium (10 ml. of a 2-M solution in hexane). Then, there is added at 20°–25° C. a solution of 3.2 g. of 5-chloro-2-methyl-3-phenylisoindole-1-carboxylic acid ethyl ester in 15 ml. of dimethylformamide, the hexane is removed by distillation and the mixture is subsequently stirred at 120° C. for 1 hour. After cooling, the mixture is poured on to 200 ml. of ice-water, the separated oil extracted with methylene chloride and the extract washed with water and evaporated to dryness. The residue is dissolved in 100 ml. of diethyl ether and the solution obtained extracted with 0.5-N hydrochloric acid. The ethereal phase contains unreacted starting material which can be recovered after concentration of the solution. The aqueous acid extract is made alkaline with concentrated ammonia solution at 0°–5° C. and the separated oil extracted with diethyl ether. The ethereal extract is washed with water, dried over sodium sulfate and concentrated to dryness. The residual base is dissolved in 5 ml. of acetone and treated with excess ethereal hydrochloric acid. The hydrochloride which crystallizes out is removed by filtration and washed with diethyl ether, and there is obtained 5-chloro-2-metyl-3-phenylisoindole-1-carboxylic acid [2-(diethylamino)ethyl]amide hydrochloride having a melting point of 211°–214° C. (decomposition).

EXAMPLE 8

Preparation of 5-chloro-2-methyl-3-phenylisoindole-1-carboxylic acid (3-aminopropyl)amide p-toluenesulfonate A suspension of 11.0 g. of 5-chloro-2-methyl-3-phenylisoindole-1-carboxylic acid (3-azidopropyl)amide and 0.6 g. of palladium/active carbon (5% palladium) in 100 ml. of ethanol is treated under an atmosphere of argon at room temperature with a solution of 1.0 g. of hydrazine hydrate in 30 ml. of ethanol and the mixture is stirred at 40° C. for 18 hours. After filtration of the catalyst, the solution obtained is concentrated to dryness under reduced pressure. The solid residue is dissolved in 50 ml. of ethanol and treated with a solution of 6.6 g. of p-toluenesulfonic acid monohydrate in 80 ml. of diethyl ether. After standing at room temperature for 1 hour, the p-toluenesulfonate which crystallizes out is removed by filtration under suction and washed with diethyl ether. 5-Chloro-2-methyl-3-phenylisoindole-1-carboxylic acid (3-aminopropyl)amide p-toluenesulfonate is obtained in the form of colorless crystals having a melting point of 203°–206° C. (decomposition). Recrystallization from ethanol does not increase the melting point.

The starting material can be prepared as follows:

54.2 G. of 7-chloro-1,3-dihydro-5-phenyl-2H,1,4-benzodiazepin-2-one are treated with 89.2 g. of (3-bromopropyl)-[tetrahydropyran-(2)] ether according to the procedure described in Example 7. There is thus obtained an oily tetrahydropyranyl derivative which is purified by chromatography on 2000 g. of silica gel using methylene chloride/ethyl acetate (2:1) for the elution and yields 7-chloro-1,3-dihydro-5-phenyl-1-{3-[(tetrahydro-2H-pyran-2-yl)oxy]propyl}-2H-1,4-benzodiazepin-2-one as a yellow oil.

41.3 G. of 7-chloro-1,3-dihydro-5-phenyl-1-{3-[(tetrahydro-2H-pyran-2-yl)oxy]-propyl}-2H-1,4-benzodiazepin-2-one, are, as described in Example 7, treated with 0.115 mol of sodium hydride and the oily rearrangement product obtained is methylated with p-toluenesulfonic acid methyl ester without further purification. The crude product is chromatographed on 1500 g. of silica gel using methylene chloride/ethyl acetate (2:1) for the elution. The homogeneous fractions are combined and concentrated to dryness. The residue crystallizes upon trituration with hexane, and there is obtained 5-chloro-2-methyl-3-phenylisoindole-1-carboxylic acid {3-[(tetrahydro-2H-pyran-2-yl)oxy]-propyl}amide having a melting point of 117°–119° C.

Recrystallization from ethyl acetate does not increase the melting point.

A solution of 12.8 g. of 5-chloro-2-methyl-3-phenylisoindole-1-carboxylic acid{3-[(tetrahydro-2H-pyran-2-yl)oxy propyl}amide in a mixture of 360 ml. of ethanol, 24 ml. of water and 6 ml. of concentrated hydrochloric acid is boiled at reflux for 3 hours. The mixture is then evaporated to dryness under reduced pressure and the residue dissolved in methylene chloride. The organic solution is washed with water and dried over sodium sulfate. After concentration, the oily residue is triturated with a small amount of ether, crystallization setting in, and there is obtained 5-chloro-2-methyl-3-phenylisoindole-1-carboxylic acid (3-hydroxypropyl)amide having a melting point of 155°–160° C. which can be used in the next step without further purification. An analytical sample is obtained by recrystallization from ethyl acetate and has a melting point of 169°–171° C.

17.0 G. of triphenylphosphine are dissolved in a mixture of 50 ml. of carbon tetrachloride and 30 ml. of dioxane, 17.1 g. of chloro-2-methyl-3-phenylisoindole-1-carboxylic acid (3-hydroxypropyl)amide are added thereto and the mixture is heated to reflux for 1 hour. After cooling, the mixture is concentrated to dryness under reduced pressure and the residue purified by chromatography on 800 g. of silica gel using methylene chloride/ethyl acetate (4:1) for the elution. The homogeneous fractions yield, after recrystallization from diethyl ether, 5-chloro-2-methyl-3-phenylisoindole-1-carboxylic acid (3-chloropropyl)amide having a melting point of 168°–171° C.

A suspension of 14.4 g. of 5-chloro-2-methyl-3-phenylisoindole-1-carboxylic acid (3-chloropropyl)amide in 80 ml. of dimethylformamide is treated with 5.2 g. of sodium azide and the mixture is stirred at 60° C. for 4 hours. The mixture is cooled and poured on to 500 ml. of ice-water. The separated product is removed by filtration under suction, washed with water and dissolved in methylene chloride. The organic solution is washed with a saturated aqueous sodium chloride solution, dried over sodium sulfate and evaporated. The solid residue is triturated with a small amount of ether and filtered, whereby there is obtained 5-chloro-2-methyl-3-phenylisoindole-1-carboxylic acid (3-azidopropyl)amide having a melting point of 143°–146° C. (decomposition) which can be used in the process without further purification. An analytical sample is obtained by recrystallization from methanol and has a melting point of 148°–150° C. (decomposition).

EXAMPLE 9

Preparation of 5-chloro-2-methyl-3-phenylisoindole-1-carboxylic acid (3-morpholinoethyl) methylamide hydrochloride A solution of 7.5 g. of 5-chloro-2-methyl-3-phenylisoindole-1-carboxylic acid (3-chloropropyl)methylamide in 40 ml. of ethyl methyl ketone is treated with 3.0 g. of sodium iodide and 1.75 g. of morpholine and the mixture is boiled at reflux for 20 hours. After concentration under reduced pressure, the residue is partitioned between water and methylene chloride, and the organic phase is washed with water, dried over sodium sulfate and concentrated to dryness. The residual oil is dissolved in 300 ml. of diethyl ether and treated with excess ethereal hydrochloric acid. The separated hydrochloride is removed by filtration, washed with diethyl ether and recrystallized from ethanol/diethyl ether, whereby there is obtained 5-chloro-2-methyl-3-phenylisoindole-1-carboxylic acid (3-morpholinoethyl)-methylamide hydrochloride in the form of almost colorless crystals having a melting point of 198°–200° C. (decomposition).

The starting material can be prepared as follows:

A suspension of 30.0 g. of 5-chloro-2-methyl-3-phenylisoindole-1-carboxylic acid methylamide in 380 ml. of dimethylformamide is treated under an atmosphere of argon with 16.8 g. of potassium tert. butylate and the mixture is stirred in an ice-bath for 15 minutes. At 10°–15° C. there is then added a solution of 44.5 g. of (3-bromopropyl) [tetrahydropyranyl-(2)] ether in 30 ml. of dimethylformamide, the mixture is then stirred at 20°–25° C. for 30 minutes and subsequently heated to 100° C. for 30 minutes. After cooling, the solvent is removed by evaporation under reduced pressure and the residue partitioned between water and methylene chloride. The organic phase is washed with water, dried over sodium sulfate and evaporated to dryness. The residual oily tetrahydropyranyl derivative is dissolved in a mixture of 120 ml. of ethanol, 80 ml. of water and 20 ml. of concentrated hydrochloric acid and the solution is boiled at reflux for 3 hours. The mixture is then evaporated to dryness under reduced pressure and the residue dissolved in methylene chloride. The organic solution is washed with a saturated aqueous sodium chloride solution and dried over sodium sulfate. After concentration, the residue is purified by chromatography on 500 g. of silica gel using methylene chloride/ethyl acetate (2:1) for the elution, and there is obtained 5-chloro-2-methyl-3-phenylisoindole-1-carboxylic acid (3-hydroxypropyl)methylamide having a melting point of 85°–88° C. which can be used in the next step without further purification. An analytical sample is obtained by recrystallization from methylene chloride/pentane and has a melting point of 92°–94° C.

A solution of 13.6 g. of triphenylphosphine in 40 ml. of carbon tetrachloride and 24 ml. of dioxane is treated with 14.3 g. of 5-chloro-2-methyl-3-phenylisoindole-1-carboxylic acid (3-hydroxypropyl)methylamide and the mixture is subsequently boiled at reflux for 1 hour. After cooling, the mixture is concentrated to dryness under reduced pressure. The residual oil is chromatographed on 800 g. of silica gel using methylene chloride/ethyl acetate (4:1) for the elution. The homogeneous fractions yield analytically pure 5-chloro-2-methyl-3-phenylisoindole-1-carboxyic acid (3-chloropropyl)methylamide as a thick yellow oil.

EXAMPLE 10

Preparation of 5-chloro-2-methyl-3-phenylisoindole-1-carboxylic acid [4 -(isopropylamino)pentyl]amide hydrochloride A solution of 5.2 ml. of isopropylamine in 25 ml. of methanol is treated with 4 ml. of 5-N methanolic hydrochloric acid. Thereafter, there are successively added under an atmosphere of argon at 20°–25° C. 3.7 g. of 5-chloro-2-methyl-3-phenylisoindole-1-carboxylic acid (4-oxopentyl)amide and 0.4 g. of sodium cyanoborohydride and the mixture is then stirred at room temperature for 48 hours. The mixture is made acidic with concentrated hydrochloric acid while cooling with ice, stirred at room temperature for an additional 0.5 hour and then concentrated to dryness under reduced pressure. The residue is made alkaline with 0.5-N sodium hydroxide with the addition of ice and extracted with 200 ml. of diethyl ether. The extract, dried over sodium sulfate, is concentrated to dryness and the residual oily base crystallized from hot hexane. The thus obtained colorless base, which melts at 102°–105° C. is dissolved in 30 ml. of acetone and treated with excess ethereal hydrochloric acid. The separated hydrochloride is removed by filtration and washed with acetone, and there is obtained 5-chloro-2-methyl-3-phenylisoindole-1-carboxylic acid [4-(isopropylamino)pentyl]amide hydrochloride in the form of colorless crystals having a melting point of 216°–218° C. (decomposition). Recrystallization from acetone/methanol does not increase the melting point.

The starting material can be prepared as follows:

A solution of 54.2 g. of 7-chloro-1,3-dihydro-5-phenyl-2H-1,4-benzodiazepin-2-one in 500 ml. of dimethylformamide is treated under an atmosphere of argon at 0° C. with 32.8 g. of potassium tertiary butylate and the mixture is then stirred in an ice-bath for 30 minutes. Then, at 10°–15° C. there is added a solution of 66 g. of 2-(3-chloropropyl)2-methyl-1,3-dioxolan in 100 ml. of dimethylformamide, the mixture is stirred at 20°–24° C. for 30 minutes and subsequently heated to 100° C. for 30 minutes. The mixture is cooled and poured on to 2.5 liters of ice-water. The separated oily product is extracted with methylene chloride and the organic phase washed with a saturated aqueous sodium chloride solution, dried over sodium sulfate and concentrated to dryness. The residue crystallizes upon trituration with ether, and there is obtained 7-chloro-1,3-dihydro-1-[3-(2-methyl-1,3-dioxolan-2-yl)propyl]-5-phenyl-2H-1,4-benzodiazepin-2-one having a melting point of 152°–153° C. Recrystallization from ethanol does not increase the melting point.

A solution of 40.0 g. of 7-chloro-1,3-dihydro-1-[3-(2-methyl-1,3-dioxolan-2-yl)propyl]-5-phenyl-2H-1,4-benzodiazepin-2-one in 500 ml. of dimethylformamide is treated under an atomsphere of argon at room temperature with 0.115 mol. of sodium hydride (5.1 g. of a 55% dispersion in mineral oil). The mixture is warmed to 60° C. over a period of about 30 minutes, then stirred at this temperature for 1 hour and thereafter at 70° C. for an additional hour. After cooling, 10 ml. of water are added dropwise and the mixture is poured on to 4 liters of ice-water. After the addition of 150 g. of sodium chloride, the separated product is removed by filtration, washed with water and dissolved in methylene chloride. The organic solution is dried over sodium sulfate and concentrated to dryness. The residue is chromatographed on 1000 g. of silica gel using methylene chloride/ethyl acetate (4:1) for the elution. The homogeneous fractions are combined and evaporated. The residual oil crystallizes upon trituration with hexane, and there is obtained 5-chloro-3-phenylisoindole-1-carboxylic acid [3-(2-methyl-1,3-dioxolan-2-yl)propyl]amide in the form of yellowish crystals having a melting point of 157°–159° C. Recrystallization from ethanol does not increase the melting point.

A solution of 24.0 g. of 5-chloro-3-phenylisoindole-1-carboxylic acid [3-(2-methyl-1,3-dioxolan-2-yl)-propyl]amide in 160 ml. of dimethylformamide is treated under an atmosphere of argon at 0°–5° C. with a solution of 2.1 g. of sodium in 40 ml. of methanol. The mixture is then stirred at room temperature for 30 minutes and subsequently added dropwise to a solution of 18.6 g. of p-toluenesulfonic acid methyl ester in 20 ml. of dimethylformamide. The mixture is subsequently stirred at room temperature for 30 minutes and then at 80° C. for 1 hour. After cooling, the mixture is poured on to 400 ml. of ice-water and, after the addition of 20 g. of sodium chloride, the separated product is removed by filtration under suction, washed with water and then dissolved in methylene chloride. The organic phase is washed with water, dried over sodium sulfate and evaporated to dryness. The residue obtained is chromatographed on 500 g. of silica gel using methylene chloride/ethyl acetate (4:1) for the elution. The uniform fractions are combined and evaporated, and there is obtained 5-chloro-2-methyl-3-phenylisoindole-1-carboxylic acid [3-(2-methyl-1,3-dioxolan-2-yl)-propyl]amide having a melting point of 137°–139° C. Recrystallization from ethanol yields colorless crystals of the same melting point.

A suspension of 8.3 g. of 5-chloro-2-methyl-3-phenylisoindole-1-carboxylic acid [3-(2-methyl-1,3-dioxolan-2-yl)propyl]amide in a mixture of 40 ml. of dioxane and 10 ml. of water is treated with 2 ml. of concentrated hydrochloric acid and then boiled at reflux for 3 hours. The solution obtained is concentrated to dryness under reduced pressure and the residue triturated with diethyl ether, and there is obtained 5-chloro-2-methyl-3-phenylisoindole-1-carboxylic acid (4-oxopentyl)amide having a melting point of 128°–131° C. which can be used in the process without further purification. An analytical sample is obtained by recrystallization from ethanol and has a melting point of 136°–138° C.

EXAMPLE 11

Preparation of 5-chloro-3-phenylisoindole-1-carboxylic acid 2-morpholinoethyl ester hydrochloride A solution of 19.7 g. of 7-chloro-2,3-dihydro-1methyl-2-oxo-5-phenyl-1H-1,4-benzodiazepine-3-carboxylic acid 2-morpholinoethyl ester in 200 ml. of dimethylformamide is treated under an atmosphere of argon at 0° C. with 0.10 mol of sodium hydride (4.4 g. of a 55% dispersion in mineral oil) and the mixture is stirred at room temperature for 30 minutes. The mixture is then warmed to 100° C. over a period of about 30 minutes and then stirred at this temperature for 1 hour. After cooling, 12 ml. of water are added dropwise and the mixture is poured on to 600 ml. of ice-water. After the addition of 30 g. of sodium chloride, the separated product is extracted with methylene chloride. The organic phase is washed with water, dried over sodium sulfate and concentrated to dryness. For purification, the solid residue obtained is boiled for about 10 minutes in 50 ml. of acetonitrile and then cooled in an ice-bath. The crude base is removed by filtration, taken up in methylene chloride and treated with excess ethereal hydrochloric acid. After the addition of diethyl ether, there is obtained 5-chloro-3-phenylisoindole-1-carboxylic acid 2-morpholinoethyl ester hydrochloride in the form of greenish crystals which melt at 240°–242° C. (decomposition). Recrystallization from methanol/diethyl ether does not increase the melting point.

The starting material can be prepared as follows:

26.2 G. of N-(2-hydroxyethyl)morpholine are treated with 8.0 g. of sodium methylate and the methanol formed is evaporated at 45° C. under reduced pressure. A solution of 35.7 g. of 7-chloro-2,3-dihydro-1-methyl-2-oxo-5-phenyl-1H-1,4-benzodiazepine-3-carboxylic acid ethyl ester in 125 ml. of methylene chloride is then added and the mixture is stirred at room temperature for 15 minutes. Then, the mixture is concentrated to dryness under reduced pressure at 40° C. and the residue suspended three times in benzene and again concentrated to dryness. The residue thus obtained is once again suspended in 100 ml. of benzene, the orange colored suspension treated dropwise with 8 ml. of glacial acetic acid and subsequently stirred until decolorized. Thereafter, the mixture is washed once with 2-N sodium carbonate solution and three times with water. The clear benzene solution obtained is shaken well with 100 ml. of 0.5-N hydrochloric acid. The hydrochloride which crystallizes out is removed by filtration under suction, treated with excess 2-N sodium carbonate solution and the liberated base extracted with methylene chloride. The separated aqueous phase is made alkaline with 2-N sodium carbonate solution and extracted with methylene chloride. The methylene chloride extracts are combined, washed with water, dried over sodium sulfate and concentrated to dryness. The oily residue crystallizes upon trituration with heptane, and there is obtained 7-chloro-2,3-dihydro-1-methyl-2-oxo-5-phenyl-1H-1,4-benzodiazepine-3-carboxylic acid 2-morpholinoethyl ester having a melting point of 162°–166° C. which can be used in the process without further purification. An analytical sample is obtained by recrystallization from ethyl acetate/hexane and has a melting point of 167°–169° C. After separation of the aqueous phase, the benzene phase is washed with water, dried over sodium sulfate and concentrated to dryness. Starting material is recovered upon trituration with heptane.

In an analogous manner the following isoindole derivatives are prepared:

| Benzodiazepine derivative | Isoindole derivative |
| --- | --- |
| 7-Chloro-2,3-dihydro-1-methyl-2-oxo-5-phenyl-1H-1,4-benzodiazepine-3-carboxylic acid 2-(dimethylamino)ethyl ester; melting point 131° – 132° C. | 5-Chloro-3-phenylisoindole-1-carboxylic acid 2-(dimethylamino)ethyl ester hydrochloride; melting point 223° – 225° C. (decomposition). |
| 7-Chloro-2,3-dihydro-1-methyl-2-oxo-5-phenyl-1H-1,4-benzodiazepine-3-carboxylic acid 3-(diethylamino)propyl ester; melting point 96° – 98° C. | 5-Chloro-3-phenylisoindole-1-carboxylic acid 3-(diethylamino)propyl ester hydrochloride; melting point 248° – 251° C. (decomposition). |
| 7-Chloro-2,3-dihydro-1-methyl-2-oxo-5-phenyl-1H-1,4-benzodiazepine-3-carboxylic acid 2-(diethylamino)ethyl ester; melting point 103° – 105° C. | 5-Chloro-3-phenylisoindole-1-carboxylic acid 2-(diethylamino)ethyl ester hydrochloride; melting point 194° – 196° C. (decomposition). |

EXAMPLE 12

Preparation of 5-chloro-3-phenylisoindole-1-carboxylic acid 3-(diethylamino)propyl ester hydrochloride A solution of 0.82 g. of 5-chloro-3-phenylisoindole-1-carboxylic acid 3-[(methylsulfonyl)oxy] propyl ester in 8 ml. of acetone is treated with 2 ml. of diethylamine and the mixture is boiled at reflux for 5 hours. The mixture is then concentrated to dryness under reduced pressure and the residue partitioned between 15 ml. of water and 15 ml. of diethyl ether. The etheral phase is treated with 6 ml. of 0.5-N hydrochloric acid and the mixture shaken well. After cooling in an ice-bath, the hydrochloride which crystallizes out is removed by filtration, dried and recrystallized from methanol/diethyl ether, and there is obtained 5-chloro-3-phenylisoindole-1-carboxylic acid 3-(diethylamino)propyl ester hydrochloride having a melting point of 248°–251° C. (decomposition).

The starting material can be prepared as follows:

16.0 G. of sodium methylate are dissolved in 150 ml. of 1,3-propanediol and the methanol formed is removed by evaporation under reduced pressure at 45° C. A solution of 71.4 g. of 7-chloro-2,3-dihydro-1-methyl-2-oxo-5-phenyl-1H-1,4-benzodiazepine-3-carboxylic acid ethyl ester in 250 ml. of methylene chloride is then added and the mixture stirred at room temperature for 40 minutes. The mixture is then cautiously made acidic with glacial acetic acid and concentrated to dryness under reduced pressure. The residue is partitioned between water and methylene chloride and the organic phase washed with a saturated sodium chloride solution and dried over sodium sulfate. After concentration, the residual oil is chromatographed on 1600 g. of silica gel using methylene chloride/ethyl acetate (4:1) for the elution. From the uniform fractions, there is obtained 7-chloro-2,3-dihydro-1-methyl-2-oxo-5-phenyl-1H-1,4-benzodiazepine-3-carboxylic acid 3-hydroxypropyl ester having a melting point of 146°–148° C. Recrystallization from benzene/hexane does not increase the melting point.

A solution of 38.7 g. of 7-chloro-2,3-dihydro-1-methyl-2-oxo-5-phenyl-1H-1,4-benzodiazepine-3-carboxylic acid 3-hydroxypropyl ester in 400 ml. of 3,4-dihydro-2H-pyran is treated with 2.0 g. of p-toluenesulfonic acid monohydrate and the mixture is stirred at room temperature for 30 minutes. 500 Ml. of ether are then added and the solution is washed with 1-N ammonium hydroxide solution and then thoroughly with water. After drying over sodium sulfate and evaporation under reduced pressure, the oily residue is crystallized from diethyl ether/hexane. The tetrahydropyranyl derivative obtained is removed by filtration, washed with hexane, dried and dissolved in 500 ml. of dimethylformamide. This solution is treated under an atmosphere of argon at 0° C. with 0.35 mol of sodium hydride (15.4 g. of a 55% dispersion in mineral oil) and the mixture is stirred at room temperature for 30 minutes. The mixture is then warmed to 100° C. over a period of about 30 minutes and then stirred at this temperature for 1 hour. After the careful addition of 30 ml. of water to the cooled mixture, the resulting mixture is poured on to 1600 ml. of ice-water and left to stand overnight. The separated solid product is removed by filtration, washed with water and dissolved in methylene chloride. The organic solution is again washed with water, dried over sodium sulfate and evaporated in a vacuum. Chromatography of the residual oil on 1500 g. of silica gel using methylene chloride/ethyl acetate (4:1) for the elution yields a solid product which, for hydrolysis, is boiled at reflux for 2 hours with 300 ml. of ethanol, 20 ml. of water and 5 ml. of concentrated hydrochloric acid. The mixture is then evaporated to dryness under reduced pressure and the solid residue crystallized from ethanol, and there is obtained 5-chloro-3-phenylisoindole-1-carboxylic acid 3-hydroxypropyl ester in the form of bluish crystals which melt at 202°–204° C. (decomposition).

A suspension of 3.3 g. of 5-chloro-3-phenylisoindole-1-carboxylic acid 3-hydroxypropyl ester in a mixture of 60 ml. of methylene chloride and 5 ml. of triethylamine is treated dropwise at 15°–20° C. with a solution of 2.4 ml. of methanesulfonyl chloride in 10 ml. of methylene chloride and the mixture is stirred at room temperature for 1 hour. After dilution with 60 ml. of methylene chloride, the suspension is removed by filtration and the filtrate washed successively with water, 0.5-N hydrochloric acid, 5% sodium bicarbonate solution and again with water. After drying over sodium sulfate and evaporation of the solution, there is obtained a solid crude product which is chromatographed on 100 g. of silica gel using methylene chloride/ethyl acetate (4:1) for the elution. The uniform fractions yield 5-chloro-3-phenylisoindole-1-carboxylic acid 3-[(methylsulfonyl)oxy]propyl ester having a melting point of 155°–158° C. which can be used in the process without further purification. An analytical sample is obtained by recrystallization from ethanol, and there are obtained greenish crystals having a melting point of 159°–161° C.

EXAMPLE 13

Preparation of 5-chloro-3-phenylisoindole-1-carboxylic acid [3-(methylamino)propyl]amide 9.5 G. of 5-chloro-3-phenylisoindole-1-carboxylic acid {3-[(benzyloxycarbonyl)methylamino]propyl}amide are dissolved in 20 ml. of glacial acetic acid and 30 ml. of a solution of 33% hydrobromic acid in glacial acetic acid are added thereto. The mixture is allowed to stand at room temperature for 2 hours with occasional agitation and it is thereafter poured into 300 ml. of diethyl ether. The separated hydrobromide is removed by filtration under suction, washed with diethyl ether and treated with 200 ml. of 2-N ammonium hydroxide solution. The liberated base is extracted with methylene chloride and the extract washed with water, dried over sodium sulfate and evaporated to dryness. After crystallization of the solid residue from ethanol, there is obtained 5-chloro-3-phenylisoindole-1-carboxylic acid [3-(methylamino)propyl]amide in the form of yellowish crystals having a melting point of 162°–164° C.

The starting material can be prepared as follows:

A solution of 34.7 g. of 7-chloro-1-(3-chloropyropyl)-1,3-dihydro-5-phenyl-2H-1,4-benzodiazepin-2-one in 200 ml. of ethyl methyl ketone is treated with 22.5 g. of sodium iodide and the mixture is boiled at reflux for 5 hours. After concentration under reduced pressure, the oily residue is partitioned between methylene chloride and water, and the organic phase washed with water and dried over sodium sulfate. The methylene chloride solution (about 100 ml.) is removed by filtration, treated with 19.2 g. of methylamine and stirred at room temperature for 18 hours. The solution is then washed thoroughly with water and extracted with 2-N hydrochloric acid. The extract is made alkaline with 2-N ammonium hydroxide solution and the liberated base extracted with methylene chloride. The organic phase is washed with a 10% aqueous sodium chloride solution and dried over sodium sulfate. After evaporation of the solvent, there is obtained 7-chloro-1,3-dihydro-1-[3-(methylamino)propyl]-5-phenyl-2H-1,4-benzodiazepin-2-one as a thick oil which, for the following step, is dissolved in 250 ml. of benzene. This solution is treated successively with 21 ml. of triethylamine and 22 ml. of chlroformic acid benzyl ester and the mixture is boiled at reflux for 6 hours. After cooling, the precipitate is removed by filtration and the filtrate concentrated to dryness. The oily residue is partitioned between methylene chloride and water, and the organic phase washed successively with 2-N hydrochloric acid, water and with a 10% aqueous sodium chloride solution. The solution, dried over sodium sulfate, is evaporated to dryness and the residual oil chromatographed on 1000 g. of aluminum oxide (neutral, Brockmann, activity I) using methylene chloride/ethyl acetate (3:2) for the elution. The homogeneous fractions yield a yellow oil (the carbobenzoxy derivative) which is dissolved in 250 ml. of dimethylformamide. This solution is treated under an atmosphere of argon at room temperature with 0.09 mol of sodium hydride (4.0 g. of a 55% dispersion in mineral oil). The mixture is warmed to 60° C. over a period of about 30 minutes, then stirred at this temperature for 1 hour and thereafter at 70° C. for an additional hour. After cooling, 10 ml. of water are added dropwise and the mixture is then poured on to 2000 ml. of ice-water. After the addition of 70 g. of sodium chloride, the separated product is extracted with methylene chloride. The organic phase is washed with a saturated sodium chloride solution, dried over sodium sulfate and concentrated to dryness. The oily residue obtained is purified by chromatography on 1000 g. of silica gel using methylene chloride/ethyl acetate (4:1) for the elution, 5-chloro-3-phenylisoindole-1-carboxylic acid {3-[(benzyloxycarbonyl)methylamino]propyl} amide having a melting point of 124°-126° C. is obtained after crystallization from diethyl ether.

EXAMPLE 14

Preparation of 5-chloro-3-phenylisoindole-1-carboxylic acid [3-(morpholino)propyl]-methylamide hydrochloride.

According to the procedure described in Example 3, 4.65 g. of o-benzoyl-p-chlorophenylglyoxylic acid [3-(morpholino)propyl] methylamide hydrochloride are reacted with 1.02 g. of ammonia and 0.4 g. of sodium cyanoborohydride. The ether extract containing the free base is concentrated to dryness and the oily residue chromatographed on 200 g. of silica gel using acetone for the elution. The homogeneous fractions are combined and evaporated. The residual oily base is dissolved in diethyl ether and treated with excess ethereal hydrochloric acid. The hydrochloride which crystallizes out is recrystallized from ethanol/diethyl ether, and there is obtained 0.9 g. of 5-chloro-3-phenylisoindole-1-carboxylic acid [3-(morpholino)propyl] methylamide hydrochloride having a melting point of 194°-197° C. (decomposition).

The starting material can be prepared as follows:

86.4 G. of ceric ammonium nitrate are dissolved in 150 ml. of water and 150 ml. of glacial acetic acid. 22.5 G. of 5-chloro-2-methyl-3-phenylisoindole-1-carboxylic acid (3-chloropropyl)methylamide are added and the mixture is stirred at 80° C. for 20 minutes, the color of the solution obtained changes from orange to light yellow. After cooling, 750 ml. of ice-water are added and the separated oil is extracted with methylene chloride. The extract is washed with 2-N ammonium hydroxide and a saturated sodium chloride solution, dried over sodium sulfate and evaporated. The oily residue is chromatographed on 1000 g. of silica gel using methylene chloride/ethyl acetate (4:1) for the elution, and there are obtained 9.9 g. of o-benzoyl-p-chlorophenylglyoxylic acid (3-chloropropyl)methylamide as a yellow oil.

A solution of 7.6 g. of o-benzoyl-p-chlorophenylglyoxylic acid (3-chloropropyl)methylamide in 40 ml. of ethyl methyl ketone is treated with 3.0 g. of sodium iodide and 3.5 g. of morpholine and the mixture is boiled at reflux for 30 hours. After concentration under reduced pressure, the residue is partitioned between water and methylene chloride, the organic phase washed with water, dried over sodium sulfate and concentrated to dryness. The residual oily base is purified on 500 g. of aluminum oxide using methylene chloride/ethyl acetate (4:1) for the elution, dissolved in diethyl ether and treated with excess ethereal hydrochloric acid. The hydrochloride which crystallizes out is recrystallized from isopropanol/diethyl ether, and there is obtained 4.9 g. of o-benzoyl-p-chlorophenylglyoxylic acid [3-(morpholino)propyl] methylamide hydrochloride in the form of light yellow crystals having a melting point of 169°-172° C. (decomposition).

EXAMPLE 15

Preparation of 5-chloro-2-methyl-3-phenylisoindole-1-carboxylic acid [3-(dimethylamino)propyl]amide A suspension of 1.02 g. of 5-chloro-2-methyl-3-phenylisoindole-1-carboxylic acid (3-aminopropyl)amide p-toluenesulfonate (prepared as described in Example 8) in 10 ml. of water is treated with 2 ml. of 2-N ammonium hydroxide and the liberated base is extracted with methylene chloride. The extract is concentrated to dryness and the residue dissolved in 6 ml. of dimethylformamide. This solution is now treated under an atmosphere of nitrogen with 0.50 ml. of a 38% solution of formaldehyde in water and 0.17 ml. of an 85% solution of formic acid in water. The mixture is then heated at 120° C. for 90 minutes, cooled and poured on to 40 g. of ice-water. The pH is adjusted to 8 with 2-N sodium hydroxide and the separated product immediately extracted with methylene chloride. The organic extract is washed with water, dried and evaporated to dryness. The residue crystallizes upon trituration with diethyl ether/hexane (4:1), and there is obtained 0.30 g. of 5-chloro-2-methyl-3-phenylisoindole-1-carboxylic acid [3-(dimethylamino)propyl] amide having a melting point of 144°-147° C. Recrystallization from ethyl acetate yields colorless crystals having a melting point of 146°-148° C.

EXAMPLE 16

Preparation of 5-chloro-3-phenylisoindole-1-carboxylic acid 3-(cyclohexylamino)propyl ester hydrochloride According to the procedure described in Example 11, 18.7 g. of 7-chloro-2,3-dihydro-1-methyl-2-oxo-5-phenyl-1H-1,4-benzodiazepine-3-carboxylic acid 3-(cyclohexylamino)propyl ester are treated with 0.14 mol of sodium hydride. The methylene chloride extract containing the free base is treated with 200 ml. of 2-N hydrochloric acid and the mixture is shaken thoroughly. After cooling in an ice-bath, the hydrochloride which precipitates out is removed by filtration under suction, washed with water and diethyl ether and dried. After recrystallization from ethanol/diethyl ether, there are obtained 5.9 g. of 5-chloro-3-phenylisoindole-1-carboxylic acid 3-(cyclohexylamino)propyl ester hydrochloride in the form of felt-like crystals having a melting point of 250°-253° C. (decomposition).

The starting material can be prepared as follows:

A solution of 38.7 g. of 7-chloro-2,3-dihydro-1-methyl-2-oxo-5-phenyl-1H-1,4-benzodiazepine-3-carboxylic acid 3-hydroxypropyl ester (prepared as described in Example 12) in a mixture of 400 ml. of methylene chloride and 34.0 ml. of triethylamine is treated dropwise at 15°–20° C. with a solution of 16.0 ml. of methanesulfonyl chloride in 100 ml. of methylene chloride, and the mixture is then stirred at room temperature for 30 minutes. After dilution with 300 ml. of methylene chloride, the suspension is removed by filtration and the filtrate washed successively with water, 0.5-N hydrochloric acid, 5% sodium carbonate solution and water. After drying over sodium sulfate and evaporation of the solution, the residue is triturated with diethyl ether, and there are obtained 44.5 g. of 7-chloro-2,3-dihydro-1-methyl-2-oxo-5-phenyl-1H-1,4-benzodiazepine-3-carboxylic acid 3-[(methylsulfonyl)oxy]propyl ester having a melting point of 129°–133° C. which can be used in the following step without further purification. An analytical sample is obtained by recrystallization from benzene/hexane and forms colorless crystals having a melting point of 138°–139° C.

A solution of 7-chloro-2,3-dihydro-1-methyl-2-oxo-5-phenyl-1H-1,4-benzodiazepine-3-carboxylic acid 3-[(methylsulfonyl)oxy]propyl ester in 400 ml. of acetone is treated with 100 ml. of cyclohexylamine and the mixture is boiled at reflux for 2 hours. The mixture is then concentrated to dryness under reduced pressure and the residue dissolved in 300 ml. of benzene. After washing with water, the organic solution is shaken with an excess of 2-N hydrochloric acid. The clear aqueous phase is made alkaline with 2-N sodium carbonate solution and the liberated base extracted with benzene. The benzene extract is washed with water, dried over sodium sulfate and concentrated to dryness. The oily residue crystallizes upon trituration with diethyl ether, and there are obtained 22.4 g. of 7-chloro-2,3-dihydro-1-methyl-2-oxo-5-phenyl-1H-1,4-benzodiazepine-3-carboxylic acid 3-(cyclohexylamino)propyl ester having a melting point of 109°–111° C.

EXAMPLE 17

In an analogous manner to that described in Example 1, the following isoindole derivatives can be prepared:

The following Examples illustrate pharmaceutical preparations containing the isoindole derivatives provided by this invention:

Example A

Tablets containing the following ingredients are prepared in a known manner.

| Ingredient | Per Tablet |
|---|---|
| 3-(p-Chlorophenyl)isoindole-1-carboxylic acid [2-(diethylamino)ethyl]amide or 5-chloro-3-(p-chlorophenyl)isoindole-1-carboxylic acid [2-(diethylamino)ethyl]amide | 10.0 mg. |
| Lactose | 65.0 mg. |
| Maize Starch | 67.5 mg. |
| Talc | 6.0 mg. |
| Magnesium stearate | 1.5 mg. |
| Total Weight | 150.0 mg. |

Example B

Capsules containing the following ingredients are prepared in a known manner:

| Ingredient | Per Capsule |
|---|---|
| 3-(p-Chlorophenyl)isoindole-1-carboxylic acid [2-(diethylamino)ethyl]amide or 5-chloro-3-(p-chlorophenyl)isoindole-1-carboxylic acid [2-(diethylamino)ethyl]amide | 10.0 mg. |
| Lactose | 85.0 mg. |
| Maize Starch | 19.0 mg. |
| Talc | 5.0 mg. |
| Magnesium stearate | 1.0 mg. |
| Total Weight | 120.0 mg. |

Example C

Tablets containing the following ingredients are prepared:

| Ingredient | Per Tablet |
|---|---|
| 5-Chloro-3-phenylisoindole-1-carboxylic acid 3-(diethylamino)propyl ester hydrochloride | 5.47 mg. |
| Lactose | 57.53 mg. |
| Maize Starch | 54.00 mg. |
| Talc | 2.70 mg. |
| Magnesium Stearate | 0.30 mg. |
| Total Weight | 120.00 mg. |

The active ingredient is carefully mixed with the lactose and a portion of the maize starch and the mixture is sieved. A paste is prepared with the remainder of the maize starch and the powder mixture is processed with this paste in a known manner to give a granulate. This granulate is then dried. After admixture of the

| Benzodiazepine derivative | Isoindole derivative |
|---|---|
| 8-Chloro-1-[2-diethylamino)ethyl]-1,3-dihdyro-5-phenyl-2H-1,4-benzodiazepin-2-one; melting point 87° – 89° C. | 6-Chloro-3-phenylisoindole-1-carboxylic acid[2-(diethylamino)ethyl]amide, melting point 143° – 145° C. |
| 1-[2-(Diethylamino)ethyl]-1,3-dihydro-7-methyl-5-phenyl-2H-1,4-benzodiazepin-2-one; melting point 84° – 86° C. | 5-Methyl-3-phenylisoindole-1-carboxylic acid [2-(diethylamino)ethyl]amide; melting point 135° – 137° C. |
| 1-[2-Diethylamino)ethyl]-1,3-dihydro-5-phenyl-7-(trifluoromethyl)-2H-1,4-benzodiazepin-2-one [dihydrochloride; melting point 150° – 155° C. (decomposition)]. | 5-Trifluoromethyl-3-phenylisoindole-1-carboxylic acid [2-(diethylamino)ethyl]amide; melting point 142° – 144° C. |
| 7-Chloro-5-(3,4-dichlorophenyl)-1-[2-(diethylamino)ethyl]-1,3-dihydro-2H-1,4-benzodiazepin-2-one [dihydrochloride; melting point 205° – 207° C. (decomposition)]. | 5-Chloro-3-(3,4-dichlorophenyl)isoindole-1-carboxylic acid [2-(diethylamino)ethyl]-amide; melting point 184° –185° C. (decomposition). |
| 7-Chloro-1-[2-(diethylamino)ethyl]-1,3-dihydro-5-(p-methoxyphenyl)-2H-1,4-benzodiazepin-2-one; melting point 109° – 111° C. | 5-Chloro-3-(p-methoxyphenyl)isoindole-1-carboxylic acid [2-(diethylamino)ethyl]-amide; melting point 182° – 184° C. |
| 1-[2-(Diethylamino)ethyl]-1,3-dihydro-5-(m-trifluoromethylphenyl)-2H-1,4-benzodiazepin-2-one; melting point 58° – 60° C. | 3-(m-Trifluoromethylphenyl)isoindole-1-carboxylic acid [2-(diethylamino)ethyl]-amide; melting point 120° – 122° C. |
| 7-Chloro-1-[3-(cyclohexylamino)propyl]-1,3-dihydro-5-phenyl-2H-1,4-benzodiazepin-2-one [dihydrochloride; melting point 262° – 265° C. (decomposition)]. | 5-Chloro-3-phenylisoindole-1-carboxylic acid [3-(cyclohexylamino)propyl]amide hydrochloride; melting point 238° – 241° C. (decomposition). |
| 1-[2-(Benzylmethylamino)ethyl]-7-chloro-1,3-dihydro-5-phenyl-2H-1,4-benzodiazepin-2-one; yellowish oil. | 5-Chloro-3-phenylisoindole-1-carboxylic acid [2-(benzylmethylamino)ethyl]amide; melting point 140° – 141° C. | remaining ingredients, the mixture is pressed to tablets each weighting 120.0 mg.

Example D

| Capsules containing the following ingredients are prepared: Ingredient | Per Capsule |
|---|---|
| 5-Chloro-3-phenylisoindole-1-carboxylic acid 3-(diethylamino)propyl ester hydrochloride | 5.47 mg. |
| Lactose | 104.53 mg. |
| Maize starch | 20.0 mg. |
| Talc | 9.0 mg. |
| Magnesium Stearate | 1.0 mg. |
| Total Weight | 140.0 mg. |

For the filling of about 10,000 capsules, 10,000-fold amounts of the aforementioned ingredients are used. 54.7 G. of active ingredient are homogeneously mixed with a similar amount of lactose. This 109.4 g. of basic mixture are diluted with 109.4 g. of lactose and again homogeneously mixed. This dilution process is continued until all of the lactose has been used up. The maize starch, talc and magnesium stearate are then added and the mixture is homogeneously mixed in a suitable mixing machine. The finished mixture is filled into capsules each containing 140 mg. on a capsule filling machine.

I claim:

1. A compound of the formula

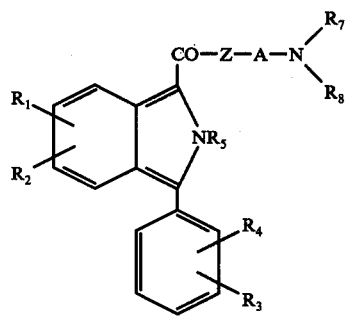

I wherein A is alkylene of 2–8 carbon atoms; Z is a group of the formula $-NR_6-$; $R_1$, $R_2$, $R_3$ and $R_4$, independently, are hydrogen, halogen, alkyl of 1 to 6 carbon atoms, alkoxy of 1 to 6 carbon atoms or trifluoromethyl; $R_5$ and $R_6$, independently, are hydrogen or alkyl of 1 to 6 carbon atoms; and $R_7$ and $R_8$, independently, are hydrogen, alkyl of 1 to 6 carbon atoms, $C_3$–$C_6$-cycloalkyl, $C_3$–$C_6$-cycloalkyl-alkyl of 1 to 6 carbon atoms, alkoxy of 1 to 6 carbon atoms-alkyl of 1 to 6 carbon atoms, phenyl, halophenyl or methoxyphenyl, or $R_7$ and $R_8$, when taken together, are a group of the formula $-(CH_2)_n-$ wherein $n$ is an integer of from 2–7, or $-NR_7R_8$ is 1-pyrrolidinyl, piperidono, morpholino or piperazino which may be substituted with alkyl of 1 to 6 carbon atoms or hydroxyalkyl of 1 to 6 carbon atoms, or a pharmaceutically acceptable acid addition salt thereof.

2. A compound in accordance with claim 1, wherein $R_1$, $R_2$, $R_3$ and $R_4$, independently, are hydrogen, halogen or trifluoromethyl.

3. A compound in accordance with claim 2, wherein $R_4$ is hydrogen, $R_1$ is chlorine, fluorine or trifluoromethyl, and $R_2$ and $R_3$, independently, are hydrogen, chlorine or fluorine.

4. A compound in accordance with claim 3, wherein $R_5$ and $R_6$, independently, are hydrogen or methyl.

5. A compound in accordance with claim 4, wherein $R_7$ and $R_8$, independently, are alkyl.

6. A compound in accordance with claim 5, wherein $R_7$ and $R_8$, independently, are ethyl or isopropyl.

7. A compound in accordance with claim 6, wherein A is ethylene or trimethylene.

8. A compound in accordance with claim 7, wherein $R_4$ is hydrogen, $R_1$ is chlorine, fluorine or trifluoromethyl, $R_2$ and $R_3$, independently, ae hydrogen, chlorine or fluorine, $R_5$ and $R_6$, independently, are hydrogen or methyl, A is ethylene or trimethylene, and $R_7$ and $R_8$, independently, are ethyl or isopropyl.

9. A compound in accordance with claim 1, 3-(p-chlorophenyl)isoindole-1-carboxylic acid [2-(diethylamino)ethyl]amide.

10. A compound in accordance with claim 1, 5-chloro-3-(p-chlorophenyl)isoindole-1-carboxylic acid [2-(diethylamino)ethyl]amide.

11. A compound in accordance with claim 1, 5-chloro-3-phenylisoindole-1-carboxylic acid [2-(diethylamino)ethyl]amide.

12. A compound in accordance with claim 1, 5,7-dichloro-3-phenylisoindole-1-carboxylic acid [2-(diethylamino)ethyl]amide.

13. A compound in accordance with claim 1, 5-chloro-3-(o-fluorophenyl)isoindole-1-carboxylic acid [2-(diethylamino)ethyl]amide.

14. A compound in accordance with claim 1, 5-chloro-3-phenylisoindole-1-carboxylic acid [3-(diethylamino)propyl] amide.

15. A compound in accordance with claim 1, 5-chloro-3-phenylisoindole-1-carboxylic acid [3-(dimethylamino)propyl] amide.

16. A compound in accordance with claim 1, 5-chloro-3-phenylisoindole-1-carboxylic acid (2-morpholinoethyl)amide.

17. A compound in accordance with claim 1, 5-chloro-3-phenylisoindole-1-carboxylic acid [2-(1-pyrrolidinyl)ethyl] amide.

18. A compound in accordance with claim 1, 5-chloro-3-phenylisoindole-1-carboxylic acid (2-piperidinoethyl)amide.

19. A compound in accordance with claim 1, 5-chloro-3-phenylisoindole-1-carboxylic acid [3-(4-methyl-1-piperazinyl)propyl] amide.

20. A compound in accordance with claim 1, 5-chloro-2-methyl-3-phenylisoindole-1-carboxylic acid [2-(diethylamino)ethyl] methylamide.

21. A compound in accordance with claim 1, 5-chloro-2-methyl-3-phenylisoindole-1-carboxylic acid [2-(diethylamino)ethyl] amide.

22. A compound in accordance with claim 1, 2-ethyl-5-chloro-3-phenylisoindole-1-carboxylic acid [2-(diethylamino)ethyl] amide.

23. A compound in accordance with claim 1, 5-chloro-3-phenylisoindole-1-carboxylic acid [2-(diethylamino)ethyl] methylamide.

24. A compound in accordance with claim 1, 5-chloro-2-methyl-3-phenylisoindole-1-carboxylic acid (3-aminopropyl)amide.

25. A compound in accordance with claim 1, 5-chloro-2-methyl-3-phenylisoindole-1-carboxylic acid (3-morpholinoethyl)methylamide.

26. A compound in accordance with claim 1, 5-chloro-2-methyl-3-phenylisoindole-1-carboxylic acid [4-(isopropylamino)pentyl] amide.

27. A compound in accordance with claim 1, 5-chloro-3-phenylisoindole-1-carboxylic acid [3-(methylamino)propyl] amide.

28. A compound in accordance with claim 1, 5-chloro-3-phenylisoindole-1-carboxylic acid [3-(morpholino)propyl] methylamide.

29. A compound in accordance with claim 1, 5-chloro-2-methyl-3-phenylisoindole-1-carboxylic acid [3-(dimethylamino)propyl] amide.

30. A compound in accordance with claim 1, 6-chloro-3-phenylisoindole-1-carboxylic acid [2-(diethylamino)ethyl] amide.

31. A compound in accordance with claim 1, 5-methyl-3-phenylisoindole-1-carboxylic acid [2-(diethylamino)ethyl] amide.

32. A compound in accordance with claim 1, 5-trifluoromethyl-3-phenylisoindole-1-carboxylic acid [2-(diethylamino)ethyl] amide.

33. A compound in accordance with claim 1, 5-chloro-3-(3,4-dichlorophenyl)-isoindole-1-carboxylic acid [2-(diethylamino)ethyl] amide.

34. A compound in accordance with claim 1, 5-chloro-3-(p-methoxyphenyl)-isoindole-1-carboxylic acid [2-(diethylamino)ethyl] amide.

35. A compound in accordance with claim 1, 3-(m-trifluoromethylphenyl)isoindole-1-carboxylic acid [2-(diethylamino)ethyl] amide.

36. A compound in accordance with claim 1, 5-chloro-3-phenylisoindole-1-carboxylic acid [3-(cyclohexylamino)propyl] amide.

37. A compound in accordance with claim 1, 5-chloro-3-phenylisoindole-1-carboxylic acid [2-(benzylmethylamino)ethyl] amide.

* * * * *

UNITED STATES PATENT AND TRADEMARK OFFICE
CERTIFICATE OF CORRECTION

PATENT NO. : 4,122,265
DATED : October 24, 1978
INVENTOR(S) : Roland Jaunin

It is certified that error appears in the above–identified patent and that said Letters Patent are hereby corrected as shown below:

Column 41, claim 1, line 53, "piperidono" should be:

piperidino

Signed and Sealed this

Twenty-fifth Day of September 1979

[SEAL]

Attest:

LUTRELLE F. PARKER
Attesting Officer    Acting Commissioner of Patents and Trademarks